US012559740B2

(12) United States Patent
Voglmeir et al.

(10) Patent No.: US 12,559,740 B2
(45) Date of Patent: Feb. 24, 2026

(54) PROCESS FOR THE DIRECT ENZYMATIC CONVERSION OF AMINO SUGARS; ENZYME AND COMPOSITIONS FOR USE IN THE PROCESS

(71) Applicant: GLYCOMICS AND GLYCAN BIOENGINEERING RESEARCH CENTER (GGBRC), NANJING AGRICULTURAL UNIVERSITY, Jiangsu (CN)

(72) Inventors: Josef Voglmeir, Jiangsu (CN); Li Liu, Jiangsu (CN)

(73) Assignee: GLYCOMICS AND GLYCAN BIOENGINEERING RESEARCH CENTER (GGBRC), NANJING AGRICULTURAL UNIVERSITY, Nanjing (CN)

( * ) Notice: Subject to any disclaimer, the term of this patent is extended or adjusted under 35 U.S.C. 154(b) by 62 days.

(21) Appl. No.: 17/917,859

(22) PCT Filed: Mar. 30, 2021

(86) PCT No.: PCT/CN2021/083999
§ 371 (c)(1),
(2) Date: Oct. 7, 2022

(87) PCT Pub. No.: WO2022/221970
PCT Pub. Date: Oct. 27, 2022

(65) Prior Publication Data
US 2024/0392278 A1     Nov. 28, 2024

(51) Int. Cl.
*C12N 9/78* (2006.01)
*C12P 3/00* (2006.01)
*C12P 19/02* (2006.01)

(52) U.S. Cl.
CPC .................. *C12N 9/78* (2013.01); *C12P 3/00* (2013.01); *C12P 19/02* (2013.01); *C12Y 305/99006* (2013.01)

(58) Field of Classification Search
CPC ... C12N 9/78; C12P 3/00; C12P 19/02; C12Y 305/99006; Y02E 50/10
See application file for complete search history.

(56) References Cited

U.S. PATENT DOCUMENTS 7,332,304 B2 * 2/2008 Deng ....................... C12P 19/26
435/325

FOREIGN PATENT DOCUMENTS

| CN | 1570589 A | 1/2005 |
| CN | 104293724 A | 1/2015 |
| CN | 105294579 A | 2/2016 |
| CN | 110714042 A | 1/2020 |
| KR | 20050069166 A | 7/2005 |
| KR | 20080063842 A | 7/2008 |
| WO | 2017174040 A1 | 10/2017 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Comb et al., Glucosamine metabolism, IV. Glucosamine-6-phosphate deaminase. J. Biol. Chem., 1958, vol. 232(2): 807-827. (Year: 1958).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Tanaka et al., Characterization of a novel glucosamine-6-phosphate deaminase from a hyperthermophilic archaeon. J. Bacteriol., 2005, vol. 187(20): 7038-7044. (Year: 2005).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Office Action for related United Kingdom Application No. GB2216714.2, dated Oct. 29, 2024, 5 pages.
Benavente et al., "Production of Glucosamine Hydrochloride from Crustacean Shell", Journal of Pharmacy and Pharmacology 3 (2015) 20-26.
Y. M. Lv et al. "Highly efficient and selective biocatalytic production of glucosamine from chitin", (2017) Green Chem., 19, 527-535).
Nishimasu et al., "Identification and Characterization of an ATP-Dependent Hexokinase with Broad Substrate Specificity from the Hyperthermophilic Archaeon Sulfolobus tokodaii", Mar. 1, 2006, J. Bacteriol. 188, 2014-2019.

(Continued)

*Primary Examiner* — Ganapathirama Raghu
(74) *Attorney, Agent, or Firm* — Stein IP, LLC

(57) ABSTRACT

A process for converting amino sugar to fructose and ammonia using one enzyme. Also provided are compositions and enzymes for converting amino sugar to fructose and ammonia.

14 Claims, 2 Drawing Sheets

Specification includes a Sequence Listing.

(56)                    References Cited

OTHER PUBLICATIONS

Bae et al., "A hexokinase with broad sugar specificity from a thermophilic bacterium", Biochemical and Biophysical Research Communications 334 (2005) 754-763.

Tanaka et al., "Characterization of a Novel Glucosamine-6-Phosphate Deaminase from a Hyperthermophilic Archaeon", American Society for Microbiology Journal of Bacteriology, vol. 187, Issue 20, Oct. 15, 2005, pp. 7038-7044.

Vincent et al., "Structure and Kinetics of a Monomeric Glucosamine 6-Phosphate Deaminase", The Journal of Biological Chemistry, vol. 280, No. 20, Issue of May 20, pp. 19649-19655, 2005.

Lee et al., "Molecular weight and some physicochemical and catalytic properties of sugar phosphate phospho hydrolase from *Escherichia coli* and neisseria meningitidis", 1975, Journal of Biological Chemistry 250(10): 3729-3737.

Maleki et al., "Identification of a New Phosphatase Enzyme Potentially Involved in the Sugar Phosphate Stress Response in Pseudomonas fluorescens", Applied and Environmental Microbiology, Jan. 2017, vol. 83, Issue 2 e02361-16, 12 pages.

Lee et al., "Sugar Phosphate Phosphohydrolase", The Journal of Biological Chemistry, vol. 242, No. 9, Issue of May 10, 1967, pp. 2264-2271.

International Search Report for related International Application No. PCT/CN2021/083999, dated Jan. 6, 2022, 6 pages.

* cited by examiner

PROCESS FOR THE DIRECT ENZYMATIC CONVERSION OF AMINO SUGARS; ENZYME AND COMPOSITIONS FOR USE IN THE PROCESS

REFERENCE TO SEQUENCE LISTING

This application includes an electronically submitted sequence listing in .txt format. The .txt file contains a sequence listing entitled "2512.1001_ST25.txt" created on Oct. 17, 2025 and is 81,043 bytes in size. The sequence listing contained in this .txt file is part of the specification and is hereby incorporated by reference herein in its entirety.

BRIEF DESCRIPTION OF THE DRAWINGS

These and/or other aspects and advantages of the invention will become apparent and more readily appreciated from the following description of the embodiments, taken in conjunction with the accompanying drawings of which.

The present invention relates to a process for converting amino sugar to fructose and ammonia using one enzyme, an enzyme for converting amino sugar to fructose and ammonia, the use of an enzyme in the conversion of at least one amino sugar into fructose and a composition for converting amino sugar to fructose and ammonia.

Fructose and ammonia are very important compounds for a vast variety of applications. It is well known in the art, that both compounds are obtainable via the indirect enzymatic conversion of glucosamine.

Glucosamine is an amino sugar and one of the most abundant monosaccharides in nature. It is the main building block of the polysaccharides chitin and chitosan. Glucosamine can be produced by the hydrolysis of chitin- or chitosan-containing biomaterials, such as shellfish exoskeletons or fungi (Benavente, M., et al. (2015) J. Pharm. Pharmacol., 3, 20-26; Lv, Y. M., et al. (2017) Green Chem., 19, 527-535).

The prior art teaches the indirect enzymatic conversion of fructose and ammonia from glucosamine involving three different classes of enzymes:

(i) sugar kinases (EC 2.7.1.2), such as the enzymes of *Sulfurisphaera tokodaii* or *Thermus caldophilus*, transfer in a first step a phosphate group from the required co-factor adenosine triphosphate (ATP) to glucosamine, yielding glucosamine 6-phosphate (Nishimasu, H., et al. (2006) J. Bacteriol. 188, 2014-2019; Bae, J., et al. (2005) Biochem. Biophys. Res. Commun. 334, 754-763);

(ii) glucosamine-6-phosphate deaminases (EC 3.5.99.6), such as the enzymes of *Thermococcus kodakarensis* or *Bacillus subtilis*, catalyze the enzymatic deamination-isomerization of glucosamine 6-phosphate to fructose-6 phosphate and ammonia (Tanaka, T., et al. (2005) J. Bacteriol. 187, 7038-7044; Vincent, F., et al. (2005) J. Biol. Chem. 280, 19649-19655); and (iii) sugar phosphatases (EC 3.1.3.23), such as the enzymes of *Escherichia coli* or *Pseudomonas fluorescens*, catalyze the hydrolysis of a phosphate group from fructose-6 phosphate to fructose (Lee, Y. P., et al. (1975) J. Biol. Chem. 250, 3729-3737; Maleki, S., et al. (2017) Appl. Environ. Microbiol. 83, e02361).

Figure 1:
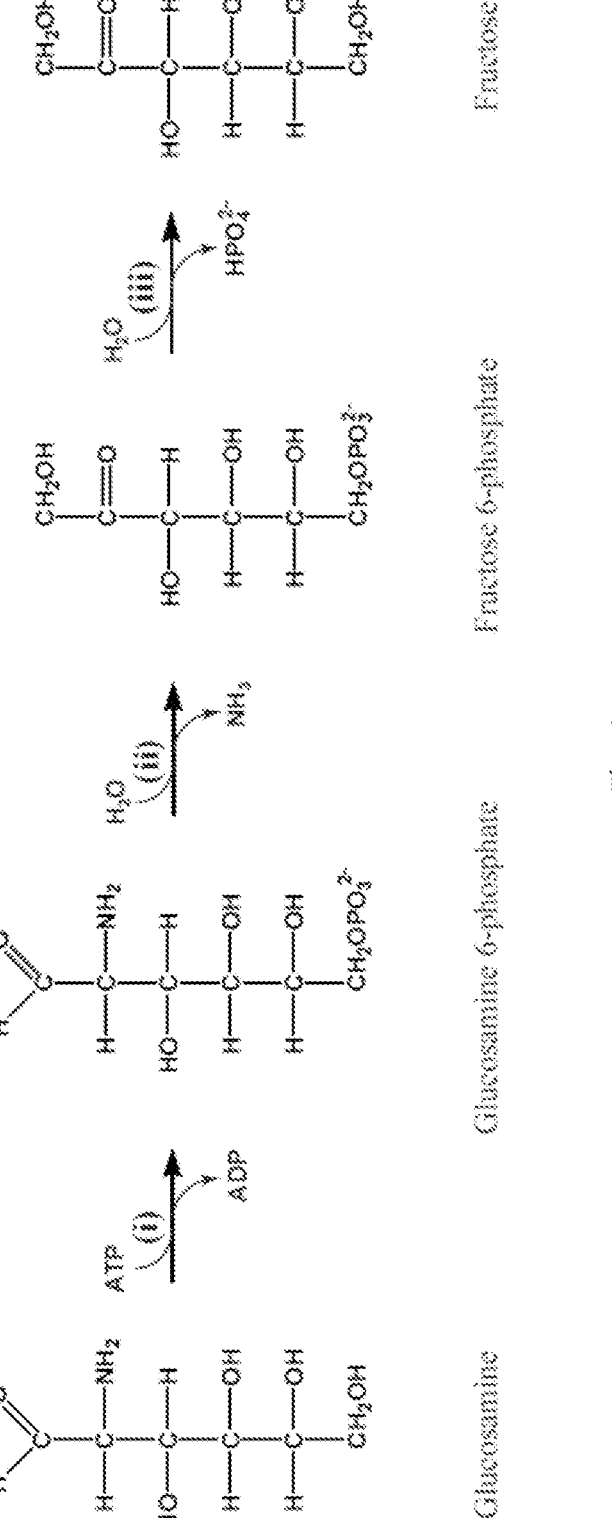
FIG. 1 schematically depicts an enzymatic process, in accordance with the state of the art, for converting glucosamine into fructose and ammonia.

FIG. 1 schematically depicts an enzymatic process, in accordance with the state art, for converting glucosamine into fructose and ammonia.

A direct enzymatic conversion from amino sugar such as glucosamine to fructose and ammonia catalyzed by one enzyme would be desirable. Such a one-step process could simplify and speed up the process. Moreover, from an ecological point of view, saving natural resources and energy would be beneficial.

In fact, despite its extremely large abundance in nature, glucosamine has not yet been used efficiently as renewable carbon source, whereas the fermentation of the resulting fructose is an established and cost-effective process in the industrial production of ethanol. Furthermore, the direct production of ammonia from glucosamine catalyzed by the GPDA (glucosamine-6-phosphate deaminase) enzyme is a desirable alternative to the existing industrial ammonia production processes.

The major challenge faced by the inventors consisted in the use of glucosamine instead of glucosamine 6-phosphate as a substrate for the GPDA enzyme-catalyzed reaction.

Therefore it is the object of the present invention to provide a direct enzymatic conversion process for the preparation of fructose and ammonia from amino sugar.

This object is solved by the present invention.

Figure 2:
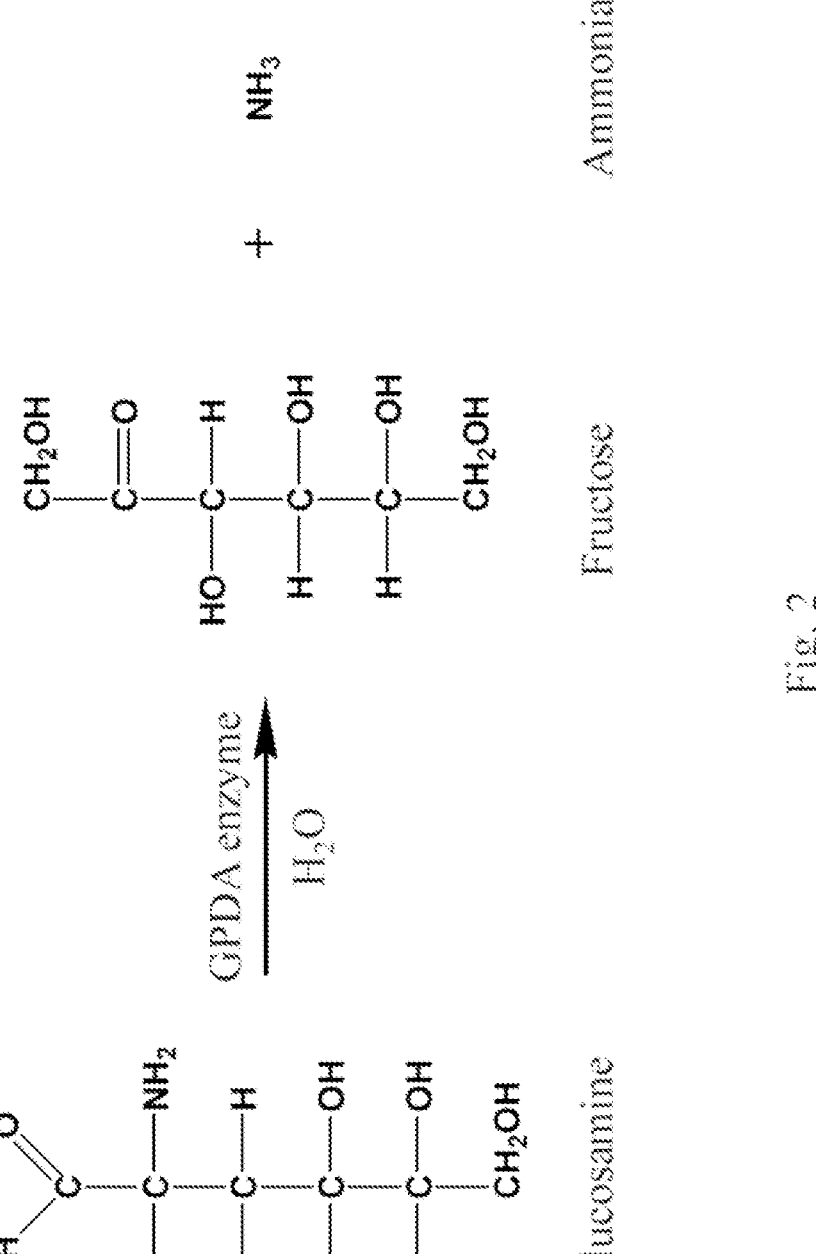
FIG. 2 schematically depicts a process for converting amino sugar to fructose and ammonia using one enzyme.

In a first aspect the present invention relates to a process for converting amino sugar to fructose and ammonia using one enzyme as schematically depicted in FIG. 2.

In a second aspect the present invention relates to an enzyme for converting amino sugar to fructose and ammonia.

In a further aspect, the present invention is directed to the use of an enzyme in the conversion of at least one amino sugar into fructose and ammonia.

In a further aspect the present invention is directed to a composition comprising ammonia and fructose obtained by a process for converting amino sugar to fructose and ammonia using one enzyme.

In another aspect the present invention relates to a composition for converting amino sugar to fructose and ammonia comprising water;

an amino sugar, preferably an amino monosaccharide, more preferably a 2-amino-2-deoxysugar and even more preferably glucosamine;

a glucosamine-6-phosphate deaminase (GPDA enzyme), preferably glucosamine-6-phosphate deaminase (GPDA enzyme) with an amino acid sequence that is at least 80%, preferably at least 90%, more preferably at least 95% and even more preferably at least 98.5% identical with the sequence according to SEQ ID NO: 1.

It has surprisingly been found that the above objective can be achieved by the use of a single enzyme.

Preferably, said single enzyme is a hydrolase, more preferably said enzyme is glucosamine-6-phosphate deaminase (GPDA enzyme), which is suitable to efficiently convert amino sugars into fructose and ammonia in an one step process.

More specifically, it has been found that a process involving only one enzyme, preferably a hydrolase, more preferably a GPDA enzyme allows for the direct conversion of amino sugars to fructose and ammonia without the need for a phosphorylation step.

The present invention provides a process for converting amino sugar to fructose and ammonia using one enzyme.

Preferably, the process is a one-step process.

Optionally, the process of the present invention further comprises a step of hydrolyzing a biomaterial, preferably a biomaterial containing amino sugars, preferably containing amino polysaccharides, more preferably containing chitin and/or chitosan.

The amino sugar is an amino monosaccharide, preferably a 2-amino-2-deoxysugar and, more preferably, the amino sugar is glucosamine.

According to an embodiment of the present invention, the amino sugar is obtained from hydrolyzing a biomaterial, preferably a biomaterial containing amino sugars, preferably containing amino polysaccharides, more preferably chitin- or chitosan-containing biomaterials, such as shellfish exoskeletons, insects or fungi.

Suitable enzymes for use in the process of the present invention include hydrolase enzymes, preferably glucosamine-6-phosphate deaminase (GPDA enzyme), such as GPDA enzyme derived from *Exiguobacterium sibiricum; Clostridium nexile; Dyadobacter fermentans; Pedobacter heparinus; Granulicella tundricola; Enterococcus faecalis; Terriglobus roseus; Akkermansia muciniphila; Bifidobacterium longum; Myxobacterium xanthis* or *Stackebrandtia nassauensis*. Preferably, the GPDA enzyme is derived from *Exiguobacterium sibiricum; Pedobacter heparinus; Granulicella tundricola; Enterococcus faecalis, Akkermansia muciniphila; Bifidobacterium longum; Myxoacterium xanthis* or *Stackebrandtia nassauensis*. Most preferably, the GPDA enzyme is Ef-GPDA from *Enterococcus faecalis*.

Several enzymes may be derived from one and the same organism of origin, in other words, homologs derived from the same organism of origin are possible. Nevertheless, such homologs are 'wild-type' variants.

The enzyme may be selected from mutant variants or "wild-type" variants. In the context of the present application, the term "wild-type" refers to the typical form of an enzyme and/or gene as it occurs in nature.

Unless otherwise indicated, all enzymes referred to herein, are "wild-type" variants.

Most preferably, the GPDA enzyme is the wild-type form of Ef-GPDA from *Enterococcus faecalis*.

The enzyme, preferably hydrolase, more preferably glucosamine-6-phosphate deaminase (GPDA enzyme) may be in the form of an isolated polypeptide or a whole-cell biocatalyst.

In some embodiments the enzyme, preferably the hydrolase, more preferably glucosamine-6-phosphate deaminase (GPDA enzyme), is immobilized.

The process according to the present invention comprises a step of contacting the glucosamine with one enzyme in the presence of water.

The enzymatic conversion achieved by the process of the present invention is a deamination-isomerization reaction.

The process according to the present invention is carried out at a temperature in a range of from 4 to 50° C., preferably from 16 to 42° C., more preferably from 30 to 42° C. and most preferably at 37° C.

The process according to the present invention is carried out at a pH in the range of from 4.0 to 10.0, preferably from 4.0 to 8.0, more preferably from 6.5 to 8.0 and most preferably at a pH of 7.0.

The process according to the present invention comprises incubating the components for at least 3 hours, preferably at least 6 hours, more preferably at least 12 hours. Preferably the maximum duration of the step of incubating the components is 96 hours, more preferably 72 hours.

In the process according to the present invention at least 10%, preferably at least 15% of the amino sugar are converted to fructose and ammonia after 24 h of enzymatic conversion.

Moreover, the process according to the present invention comprises a step of providing a composition comprising:
   water;
   an amino sugar, preferably an amino monosaccharide, more preferably a 2-amino-2-deoxysugar and even more preferably glucosamine;
   an enzyme, preferably glucosamine-6-phosphate deaminase (GPDA enzyme), more preferably the glucosamine-6-phosphate deaminase is the wild-type form of glucosamine-6-phosphate deaminase derived from *Enterococcus faecalis* (Ef-GPDA enzyme, wild-type) and/or the glucosamine-6-phosphate deaminase (GPDA enzyme) comprises an amino acid sequence that is at least 80%, preferably at least 90%, more preferably at least 95% and even more preferably at least 98.5% identical with the sequence according to SEQ ID NO: 1.

The composition according to the present invention may further comprise additives, for example, buffer solutions.

The concentration of the enzyme in the composition is in a range of from 0.2 g/L to 10 g/L.

The concentration of the amino sugar in the composition is in a range of from 1 mM to 500 mM.

If present, the concentration of a pH buffer in the composition is in a range of from 0 to 200 mM.

The concentration of, optionally contained, further additives in the composition is in a range of from 0 to 5 mM. An example of a further additive is magnesium chloride (MgCl$_2$).

The composition according to the present invention does not comprise phosphates, neither in free nor conjugated form.

The present invention further relates to an enzyme for converting amino sugar, preferably amino monosaccharide, preferably 2-amino-2-deoxysugar and more preferably glucosamine to fructose and ammonia.

Specifically, the enzyme is a hydrolase, preferably glucosamine-6-phosphate deaminase (GPDA enzyme), more preferably glucosamine-6-phosphate deaminase (GPDAenzyme) comprising an amino acid sequence that is at least 80%, preferably at least 90%, more preferably at least 95% and even more preferably at least 98.5% identical with the sequence according to SEQ ID NO: 1.

Moreover, the requirements regarding the enzyme as already pointed out above, that is in the context of the process according to the present invention, are equally applicable to the enzyme as such and vice-versa.

In a further embodiment, the present invention is directed to the use of an enzyme (as detailed above) in the conversion of at least one amino sugar, preferably 2-amino-2-deoxysugar, into fructose and ammonia.

According to a preferred embodiment, the amino sugar is obtained from hydrolyzing biomaterials, preferably chitin- or chitosan-containing biomaterials, such as shellfish exoskeletons, insects or fungi.

In a further aspect, the present invention is directed to a composition comprising ammonia and fructose obtained by a process for converting amino sugar to fructose and ammonia using one enzyme.

According to a preferred embodiment, said composition comprising ammonia and fructose does not contain phosphate, neither in free nor conjugated form.

EXPERIMENTAL PART

Analytical Methods
Ammonia Determination in Enzymatic Transformations

Reaction mixtures (50 μL) were diluted with a 1.5% (w/V) NaOH solution (930 μL). The ammonium electrode (DX218-NH4, Mettler Toledo) was then immersed into the sample until a stable reading is obtained (typically 2 min). The values were then compared with the calibration curve of ammonium standards of known concentrations between 10 μM and 1 mM.
Fructose and Glucosamine Determination in Enzymatic Transformations Using TLC.
One microliter of the enzyme reaction mixture was spotted onto a silica 60 F254 TLC plate (Merck), and the plate contents were developed using a solvent mixture of acetonitrile/acetic acid/water (7:1.5:1.5, VN/V). The developed plate contents were dried and visualized using a solvent mixture of acetone, phosphoric acid, aniline and diphenylamine (90:8:2:2, V/V/V/w), and then subjected to heating for 10 min at 120° C.

Fructose spots were observed at Rf=0.61. Glucosamine spots were observed at Rf=0.31.
Sample Derivatization for Photometric Measurement of Fructose in Enzymatic Transformations (Based on Agri. Biol. Chem. (1968) 32:6, 689-706).

Reaction mixtures (50 μL) were centrifuged at 12000 g for 10 min at room temperature, and 40 μL samples of the supernatant were taken and mixed with 35 μL conc. HCl and 5 μL of resorcinol-thiourea reagent (consisting of 0.1% (w/V) resorcinol and 0.25% (w/V) in glacial acetic acid). The mixed samples were incubated at 80° C. for 10 min and then centrifuged at 12000 g for 10 min at room temperature. The supernatants (50 μL) were then transferred to 96 microplate and the absorbance at λ=505 nm measured with a microplate photometer (Thermo Multiskan).

Activity Test Using Seliwanoff's Derivatization Method of Fructose (Photometric Resorcinol Test at λ=505 nm)
Materials Unless otherwise indicated, all materials were obtained from commercial sources.
Glucosamine Glucosamine can be obtained commercially in the form of glucosamine hydrochloride. Alternatively, glucosamine may be obtained via hydrolysis of chitin, chitosan or N-acetylglucosamine. Likewise, glucosamine may be obtained via enzymatic conversion of N-acetylglucosamine.
Hydrolysis of Chitin, Chitosan or N-Acetylglucosamine to Glucosamine Glucosamine can be prepared from chitin, chitosan, or N-acetylglucosamine using hydrochloric acid (Ainbu, A. et al. (2008) Biomacromolecules, 9, 1870-1875). Powdered chitin from shrimp shells (1 g) is suspended in 1 mL of dilute HCl (100 mM) and wettened and suspended in 50 mL of a 6 M HCl solution. This suspension is heated for 3 h at 100° C. and then cooled down to room temperature. The solution is adjusted to pH 7 via dropwise addition of NaOH solution (4 M) and dried using rotary evaporation.
Enzymatic Conversion of N-Acetylglucosamine to Glucosamine Glucosamine can be also produced enzymatically from N-acetylglucosamine (Lv, Y. M., et al. (2017) Green Chem., 19, 527-535): 50 g/L of N-acetylglucosamine are incubated at 37° C. in the presence of 120 mg/L of *Cyclobacterium marinum* N-acetylglucosamine deacetylase in 200 mM sodium phosphate buffer (pH 8.0) for 12 h. After completion of the reaction, the reaction mixture is dried using rotary evaporation.
Preparation of the GPDA Enzyme:

Genes encoding the wild-type or mutant variants of GDPA were synthesized in an *E. coli* codon-optimized form (Genscript) and delivered in a pUC19 vector with ampicillin resistance. The protein-encoding insert was cut via Ndel and Xhol restriction enzymes (Takara) and ligated in a pET30a expression vector via T4 Ligase (Takara). The GPDA enzymes were prepared as follows: a fresh single colony from an LB agar plate supplemented with 50 mg/mL Kanamycin and used to grow *E. coli* strain BL21 comprising the respective plasmid was used to inoculate 5 mL of LB liquid medium with the same concentration of Kanamycin. Following incubation of said culture over night at 120 rpm and 37° C. 2 mL of the overnight culture was used to inoculate 400 mL of the same medium in a 2 L flask. The flask was shaken at 37° C. and 120 rpm until an OD600 of 0.6 was reached, i.e. approximately two to four hours. The expression of the respective enzyme was subsequently induced by addition of 0.4 mL IPTG (Isopropyl-β-D-thiogalactopyranoside, 238 mg/mL), followed by incubation over night at 18° C. and 120 rpm under vigorous shaking. Cells were then pelleted at 4000 g and 4° C. for 20 minutes. The supernatant was disposed of, the pellet was resuspended in phosphate buffer (50 mM NaH$_2$PO$_4$, 300 mM NaCl, 10 mM Imidazole) and lysed using ultrasonication (1 s pulse followed by incubation for 4 s, repeated for a total of 20 minutes). The cell lysate was centrifuged (18000 g, 20 min, 4° C.), and applied to a His-trap column having a bed volume of 5 mL. The His-trap column was washed using phosphate buffer (50 mM $NaH_2PO_4$, 300 mM NaCl) comprising 20 mM imidazole. The GPDA enzyme was eluted by application of 10 mL of the same buffer comprising 250 mM imidazole. Fractions comprising the GPDA enzyme were pooled and then stored at −80° C., dialyzed against phosphate buffer to remove imidazole and concentrated via Vivaspin tubes and centrifugation at 4° C.

Further details regarding GPDA variants used in the examples and comparative examples are given in Table 1 below. Unless otherwise indicated, all enzymes are obtained as wild type variants from the respective organism of origin. Regarding the enzymes denoted as Es1/Es2, Ph1/Ph2/Ph3, Bl1/Bl2 and Sn1/Sn2, it is pointed out that they are homologs in the same organism of origin (descended from the same enzyme family, but probably having different physiological functions in the organism) and exclusively 'wild-type' variants.

TABLE 1

| Sample No° | Identifier | GPDA Origin | SEQ ID NO |
|---|---|---|---|
| 1 | Ef | *Enterococcus faecalis* | 1 (AA)/2 (DNA) |
| 2 | Es1 | *Exiguobacterium sibiricum* | 3 (AA)/4 (DNA) |
| 3 | Es2 | *Exiguobacterium sibiricum* | 5 (AA)/6 (DNA) |
| 4 | Cn | *Clostridium nexile* | 7 (AA)/8 (DNA) |
| 5 | Df | *Dyadobacter fermentans* | 9 (AA)/10 (DNA) |
| 6 | Ph1 | *Pedobacter heparinus* | 11 (AA)/12 (DNA) |
| 7 | Ph2 | *Pedobacter heparinus* | 13 (AA)/14 (DNA) |
| 8 | Ph3 | *Pedobacter heparinus* | 15 (AA)/16 (DNA) |
| 9 | Gt | *Granulicella tundricola* | 17 (AA)/18 (DNA) |
| 10 | Tr | *Terriglobus roseus* | 19 (AA)/20 (DNA) |
| 11 | Am | *Akkermansia muciniphila* | 21 (AA)/22 (DNA) |
| 12 | Bl1 | *Bifidobacterium longum* | 23 (AA)/24 (DNA) |
| 13 | Bl2 | *Bifidobacterium longum* | 25 (AA)/26 (DNA) |
| 14 | Mx | *Myxobacterium xanthis* | 27 (AA)/28 (DNA) |
| 15 | Sn1 | *Stackebrandtia nassauensis* | 29 (AA)/30 (DNA) |
| 16 | Sn2 | *Stackebrandtia nassauensis* | 31 (AA)/32 (DNA) |
| 17 | Ef-Ser74Ala | Mutant variant - derived from *Enterococcus faecali* | 33 (AA)/34 (DNA) |
| 18 | Ef-Thr144Ala | Mutant variant - derived from *Enterococcus faecalis* | 35 (AA)/36 (DNA) |

Working Examples

Enzymatic Generation of Ammonia by Ef-GPDA:

The enzymatic reaction mixtures consisting of 30 µL of purified Ef-GPDA solution (1.8 mg/mL), 35 µL of MES buffer (500 mM, pH 7.0), 5 µL of $MgCl_2$ (30 mM), and 30 µL of glucosamine (concentration range between 3 and 140 mM). Samples were incubated at 40° C. for 10 h. The ammonia concentration was measured potentiometrically using an ammonia gas sensing electrode.

TABLE 2

| | Glucosamine Conc. [mM] | | | | | | | |
|---|---|---|---|---|---|---|---|---|
| | 1 | 2 | 3 | 5 | 6 | 8 | 10 | 15 |
| $NH_3$ Conc. [mM] | 0.45 | 0.59 | 0.69 | 0.98 | 1.32 | 1.50 | 2.01 | 2.60 |

Activity of Ef-GPDA at Different pH Values:

Enzymatic reaction mixtures consisting of 30 µL of purified Ef-GPDA solution (1.8 mg/mL), 5 µL of $MgCl_2$ (30 mM), and 30 µL of glucosamine (15 mM) and 35 µL of the following buffer solutions:

Tris/HCl buffer (500 mM) for pH values 4.0, 5.0, 6.0, 7.0, and 8.0, Bicine buffer (500 mM) for pH 9.0, and Carbonate/Bicarbonate buffer (500 mM) for pH 10.

Samples were incubated at 40° C. for 10 h. The conversion of glucosamine to fructose was measured photometrically at $\lambda=505$ nm after samples were derivatized with resorcinol.

TABLE 3

| | pH | | | | | | |
|---|---|---|---|---|---|---|---|
| | 4.0 | 5.0 | 6.0 | 7.0 | 8.0 | 9.0 | 10.0 |
| Glucosamine to Fructose Conversion [%] | 6.8 | 6.8 | 5.5 | 12.8 | 9.4 | 3.0 | 3.5 |

Activity of Ef-GPDA at Different Temperatures:

The enzymatic reaction mixtures consisting of 30 µL of purified Ef-GPDA solution (1.8 mg/mL), 35 µL of MES buffer (500 mM, pH 7.0), 5 µL of $MgCl_2$ (30 mM), and 30 µL of glucosamine (15 mM). Samples were incubated at various temperatures between 4° C. and 50° C. for 6 h. The conversion of glucosamine to fructose was measured photometrically at $\lambda=505$ nm after samples were derivatized with resorcinol.

TABLE 4

| | Temperature [° C.] | | | | | | | | |
|---|---|---|---|---|---|---|---|---|---|
| | 4 | 10 | 16 | 20 | 25 | 30 | 37 | 42 | 50 |
| Glucosamine to Fructose Conversion [%] | 2.1 | 1.4 | 2.6 | 0.9 | 4.2 | 5.2 | 8.2 | 5.3 | 0.4 |

Temperature Stability of Ef-GPDA:

The temperature stability of Ef-GPDA was determined by incubating the enzyme at 4° C., 30° C., 37° C., 42° C., and 50° C. for periods of 0 h, 2 h, 4 h, 6 h, 12 h, 24 h, and 48 h. Then, these enzyme solutions were used in enzymatic reaction mixtures consisting of 30 µL of purified Ef-GPDA solution (1.8 mg/mL), 35 µL of MES buffer (500 mM, pH 7.0), 5 µL of $MgCl_2$ (30 mM), and 30 µL of glucosamine (concentration range between 3 and 140 mM). Samples were incubated at 40° C. for 6 h. The conversion of glucosamine to fructose was measured photometrically at $\lambda=505$ nm after samples were derivatized with resorcinol.

TABLE 5

| | | Time [h] | | | | | |
| | | 0 | 2 | 4 | 6 | 12 | 24 | 48 |
|---|---|---|---|---|---|---|---|---|
| Glucosamine to | T = 4° C. | 10.15 | 9.87 | 9.78 | 9.67 | 8.64 | 9.36 | 7.49 |
| Fructose Conversion | T = 30° C. | 10.15 | 9.37 | 8.38 | 8.42 | 9.11 | 8.20 | 8.95 |
| [%] | T = 37° C. | 10.15 | 8.64 | 8.76 | 8.42 | 8.64 | 6.97 | 7.49 |
| | T = 42° C. | 10.15 | 6.75 | 4.33 | 4.08 | 3.70 | 0.80 | 1.44 |
| | T = 50° C. | 10.15 | 4.02 | 3.17 | 2.01 | 1.17 | 0.80 | N/A |

Kinetic Parameters of Ef-GPDA:

For the kinetic analysis enzymatic reaction mixtures consisting of 30 μL of purified Ef-GPDA solution (1.8 mg/mL), 35 μL of MES buffer (500 mM, pH 7.0), 5 μL of $MgCl_2$ (30 mM), and 30 μL of glucosamine (concentration range between 3 and 140 mM). Samples were incubated at 40° C. for 10 h. The conversion of glucosamine to fructose was measured photometrically at $\lambda$=505 nm after samples were derivatized with resorcinol.

Vmax=4.0±0.2 μmol/min
Km=21.8±2.3 mM

Comparison of the Activity of Various GPDA Genes Towards Glucosamine:

Enzymatic reaction mixtures consisting of 30 μL of purified GPDA protein variants (1.8 mg/mL), 35 μL of MES buffer (500 mM, pH 7.0), 5 μL of $MgCl_2$ (30 mM), and 30 μL of glucosamine (15 mM). Samples were incubated at 40° C. for 10 h. The conversion rate of glucosamine to fructose was measured photometrically at $\lambda$=505 nm after samples were derivatized with resorcinol.

TABLE 8

| | GPDA - Enzyme Variant | | | | | | | |
| | Es1 | Cn | Df | Ph1 | Ph2 | Ph3 | Sn1 | Gt |
|---|---|---|---|---|---|---|---|---|
| Relative conversion rate [%] | 5.4 | 0.0 | 0.0 | 0.0 | 0.7 | 3.4 | 1.3 | 5.4 |

| | GPDA - Enzyme Variant | | | | | | | |
| | Ef | Sn2 | Es2 | Tr | Am | Bl1 | Mx | Bl2 |
|---|---|---|---|---|---|---|---|---|
| Relative conversion rate [%] | 100 | 1.3 | 0.0 | 0.0 | 0.7 | 3.4 | 4.0 | 0.0 |

TABLE 6

| | Glucosamine Conc. [mM] | | | | | | |
| | 1 | 5 | 10 | 15 | 25 | 35 | 45 |
|---|---|---|---|---|---|---|---|
| Reaction Velocity [μM/min] | 0.17 | 0.72 | 1.35 | 1.74 | 1.98 | 2.45 | 2.68 |

Timecourse Experiment to Determine the Activity of Ef-GPDA:

Enzymatic reaction mixtures consisting of 30 μL of purified Ef-GPDA solution (1.8 mg/mL), 35 μL of MES buffer (500 mM, pH 7.0), 5 μL of $MgCl_2$ (30 mM), and 30 μL of glucosamine (15 mM). Samples were incubated at 40° C. for up to 24 h. The conversion of glucosamine to fructose was measured photometrically at $\lambda$=505 nm after samples were derivatized with resorcinol.

Gpda Origin:

Es1, Es2: *Exiguobacterium sibiricum*; Cn: *Clostridium nexile*; Df: *Dyadobacter fermentans*; Ph1, Ph2, Ph3: *Pedobacter heparinus*; Gt: *Granulicella tundricola*; Ef: *Enterococcus faecalis*; Tr: *Terriglobus roseus*; Am: *Akkermansia muciniphila*; Bl1, Bl2: *Bifidobacterium longum*; Mx: *Myxobacterium xanthis*; Sn1, Sn2: *Stackebrandtia nassauensis*.

Ef-GPDA Wild-Type and Mutant Variants

Ef-GPDA mutant variants were generated and tested for enzymatic activity following the same test protocol as detailed above for GPDA variants originating from different organisms.

The mutant variants of Ef-GPDA were selected based on studies of the glucosamine-6-phosphate deaminase family (i.e from the *E. coli* variant).

TABLE 7

| | Time of Enzymatic Reaction [h] | | | | |
| | 3.5 | 6 | 12 | 17 | 23 |
|---|---|---|---|---|---|
| Glucosamine to Fructose Conversion [%] | 2.51 | 3.44 | 8.24 | 10.57 | 16.84 |

TABLE 9

| | Ef-GPDA Enzyme Variant | | |
| | Ser74Ala | Thr144Ala | Wild Type |
|---|---|---|---|
| Relative Enzymatic Activity [%] | 107.7 | 103.5 | 100 |

The invention claimed is:

1. A process for converting amino sugar to fructose and ammonia, the steps of which consist of:
   optionally hydrolyzing a biomaterial comprising amino sugars; and
   converting the amino sugars to fructose and ammonia via a single type of enzyme consisting of glucosamine-6-phosphate deaminase (GPDA), wherein the enzyme comprises the amino acid sequence selected from the group consisting of: SEQ ID NO:33 and SEQ ID NO:35; and
   wherein the amino sugars are glucosamine.

2. The process according to claim 1, wherein the glucosamine-6-phosphate deaminase (GPDA enzyme) is an isolated polypeptide or a whole-cell biocatalyst.

3. The process according to claim 1, wherein at least 10% of the amino sugars are converted to fructose and ammonia after 24 hours of enzymatic conversion.

4. The process according to claim 1, wherein the process is a one-step process.

5. The process according to claim 1, wherein the amino sugars are obtained from hydrolyzing chitin- or chitosan-containing biomaterials.

6. The process according to claim 1, wherein in said step the glucosamine is contacted with the GPDA in the presence of water.

7. The process according to claim 1, wherein the enzyme is immobilized.

8. The process according to claim 1, wherein the biomaterial comprises amino polysaccharides.

9. The process according to claim 1, wherein the converting is a deamination-isomerization reaction.

10. An enzyme for converting glucosamine to fructose and ammonia, wherein the enzyme comprises the amino acid sequence selected from the group consisting of: SEQ ID NO:33 and SEQ ID NO:35.

11. A composition for converting amino sugar to fructose and ammonia, comprising:
   water;
   an amino sugar;
   glucosamine-6-phosphate deaminase (GPDA) comprising the amino acid sequence selected from the group consisting of: SEQ ID NO:33 and SEQ ID NO:35;
   wherein the amino sugar is glucosamine.

12. The process according to claim 3, wherein at least 15% of the amino sugars are converted to fructose and ammonia after 24 hours of enzymatic conversion.

13. The process according to claim 5, wherein the chitin- or chitosan-containing biomaterials comprise shellfish exoskeletons, insects, and fungi.

14. The process according to claim 8, wherein the biomaterial comprises chitin or chitosan.

* * * * *

SEQUENCE LISTING

<160> NUMBER OF SEQ ID NOS: 36

<210> SEQ ID NO 1
<211> LENGTH: 233
<212> TYPE: PRT
<213> ORGANISM: Enterococcus faecalis

<400> SEQUENCE: 1

Met Gln Ile Ile Arg Val Ala Asn Ala Glu Glu Gly Gly Lys Lys Ala
1               5                   10                  15

Phe Glu Leu Ile Lys Glu Gly Met Asn Asn Gly Ala Lys Val Leu Gly
            20                  25                  30

Leu Ala Thr Gly Ser Thr Pro Glu Thr Leu Tyr Lys Glu Met Thr Ala
        35                  40                  45

Ser Asp Ile Asp Phe Thr Glu Met Thr Ser Val Asn Leu Asp Glu Tyr
    50                  55                  60

Val Gly Leu Gly Gly Glu Asp Glu Gln Ser Tyr Arg Tyr Phe Met Asn
65                  70                  75                  80

Lys His Leu Phe Asp Lys Lys Pro Phe Lys Glu Thr Phe Val Pro Asn
                85                  90                  95

Gly Lys Ala Glu Asp Leu Asp Ala Ala Ser Ala Glu Tyr Glu Lys Ile
                100                 105                 110

Ile Asp Ala His Pro Val Asp Ile Gln Ile Leu Gly Ile Gly Gln Asn
            115                 120                 125

Gly His Ile Gly Phe Asn Glu Pro Gly Thr Pro Leu Asp Ser Leu Thr
        130                 135                 140

His Val Val Glu Leu Thr Glu Ser Thr Ile Asn Ala Asn Lys Arg Tyr
145                 150                 155                 160

Phe Asp Lys Val Glu Asp Val Pro Thr Arg Ala Val Ser Met Gly Ile
                165                 170                 175

Gly Ser Ile Met Lys Gly Lys Lys Met Ile Leu Met Ala Tyr Gly Glu
            180                 185                 190

Ala Lys Ala Glu Ala Ile Lys Gly Met Ile Asp Gly Pro Val Thr Thr
        195                 200                 205

Asp Met Pro Ala Ser Ala Leu Gln Asn His Gln Asp Val Val Val Ile
    210                 215                 220

Ile Asp Asp Ala Ala Ala Ser Lys Leu
225                 230

<210> SEQ ID NO 2
<211> LENGTH: 702
<212> TYPE: DNA
<213> ORGANISM: Enterococcus faecalis

<400> SEQUENCE: 2
atgcagatca tccgtgttgc taacgctgaa gaaggtggta aaaaagcttt cgaactgatc      60
aaagaaggta tgaacaacgg tgctaaagtt ctgggtctgg ctaccggttc taccccggaa     120
accctgtaca agaaatgac cgcttctgac atcgacttca ccgaaatgac ctctgttaac      180
ctggacgaat acgttggtct gggtggtgaa gacgaacagt cttaccgtta cttcatgaac     240
aaacacctgt tcgacaaaaa accgttcaaa gaaaccttcg ttccgaacgg taaagctgaa     300
gacctggacg ctgcttctgc tgaatacgaa aaaatcatcg acgctcaccc ggttgacatc     360
cagatcctgg gtatcggtca gaacggccat atcggcttca cgaaccgggg cacccccgctg     420 gactctctga cccacgttgt tgaactgacc gaatctacca tcaacgctaa caaacgttac     480
ttcgacaaag ttgaagacgt tccgacccgt gctgtttcta tgggtatcgg ttctatcatg     540
aaaggtaaaa aaatgatcct gatggcttac ggtgaagcta aagctgaagc tatcaaaggt     600
atgatcgacg tccggttac accgacatg ccggcttctg ctctgcagaa ccaccaggac     660
gttgttgtta tcatcgacga cgctgctgct tctaaactgt aa                        702

<210> SEQ ID NO 3
<211> LENGTH: 252
<212> TYPE: PRT
<213> ORGANISM: Exiguobacterium sibiricum
<220> FEATURE:
<221> NAME/KEY: misc_feature
<223> OTHER INFORMATION: Es1 Variant

<400> SEQUENCE: 3

Met Lys Trp Met Ile Val Glu Lys Ala Glu Glu Leu Ala Asn Val Ser
1               5                   10                  15

Tyr Gln Leu Leu Lys Gln Glu Ile Val Arg His Pro Glu Gly Leu Thr
            20                  25                  30

Ile Gly Leu Ala Thr Gly Ser Ser Pro Leu Gly Val Tyr Glu Glu Trp
        35                  40                  45

Arg Lys Asp Arg Val Asp Cys Arg His Val Thr Thr Val Asn Leu Asp
    50                  55                  60

Glu Tyr Val Gly Leu Ser Pro Asp His Pro His Ser Tyr His Thr Phe
65                  70                  75                  80

Met Gln Glu His Leu Phe Asp Ala Val Asp Phe Lys Glu Ser Tyr Val
                85                  90                  95

Pro Ile Gly Ser Thr Ala Asp Pro Arg Glu Glu Ser Asp Arg Tyr Glu
            100                 105                 110

Ala Leu Val Arg Gln Leu Gly Ile Asp Ile Gln Leu Leu Gly Ile Gly
        115                 120                 125

Ser Asn Gly His Ile Ala Phe Asn Glu Pro Gly Thr Pro Phe Asp Ala
    130                 135                 140

Lys Thr His Val Thr Lys Leu Thr Glu Ser Thr Arg Gln Ala Asn Gln
145                 150                 155                 160

Arg Phe Phe Asp Arg Leu Glu Asp Val Pro Thr Glu Ala Ile Thr Met
                165                 170                 175

Gly Ile Gly Thr Ile Met Glu Ala Lys Lys Ile Leu Leu Val Ala Ser
            180                 185                 190

Ser Glu Arg Lys Ala Glu Ala Ile Arg Asp Met Met Glu Gly Pro Ala
        195                 200                 205

Thr Thr Asp Cys Pro Ala Thr Ile Leu Gln Arg His Ala Asp Val Met
    210                 215                 220

Val Val Leu Asp Glu Glu Ala Ala Ser Leu Leu Ser Asp Glu Ala Lys
225                 230                 235                 240

Arg Thr Gly Arg Ala Ala Tyr Thr Asn Phe Met Lys
                245                 250

<210> SEQ ID NO 4
<211> LENGTH: 759
<212> TYPE: DNA
<213> ORGANISM: Exiguobacterium sibiricum
<220> FEATURE:
<221> NAME/KEY: misc_feature
<223> OTHER INFORMATION: Es1 Variant

<400> SEQUENCE: 4
atgaaatgga tgatcgttga aaaagctgaa gaactggcta acgtttctta ccagctgctg     60

```
aaacaggaaa tcgttcgtca cccggaaggt ctgaccatcg gtctggctac cggttcttct        120
ccgctgggtg tttacgaaga atggcgtaaa gaccgtgttg actgccgtca cgttaccacc        180
gttaacctgg acgaatacgt tggtctgtct ccggaccacc cgcactctta ccacaccttc        240
atgcaggaac acctgttcga cgctgttgac ttcaaagaat cttacgttcc gatcggttct        300
accgctgacc cgcgtgaaga atctgaccgt tacgaagctc tggttcgtca gctgggtatc        360
gacatccagc tgctgggtat cggttctaac ggccatatcg cgttcaacga accgggcacc        420
ccgttcgacg ctaaaaccca cgttaccaaa ctgaccgaat ctacccgtca ggctaaccag        480
cgtttcttcg accgtctgga agacgttccg accgaagcta tcactatggg tatcggtacc        540
atcatggaag ctaaaaaaat cctgctggtt gcttcttctg aacgtaaagc tgaagctatc        600
cgtgacatga tggaaggtcc ggctaccacc gactgcccgg ctaccatcct gcagcgtcac        660
gctgacgtta tggttgttct ggacgaagaa gctgcttctc tgctgtctga cgaagctaaa        720
cgtaccggtc gtgctgctta caccaacttc atgaaataa                              759
```

<210> SEQ ID NO 5
<211> LENGTH: 598
<212> TYPE: PRT
<213> ORGANISM: Exiguobacterium sibiricum
<220> FEATURE:
<221> NAME/KEY: misc_feature
<223> OTHER INFORMATION: Es2 Variant

<400> SEQUENCE: 5

```
Met Cys Gly Ile Val Gly Met Ile Gly Gln Val Asn Thr Lys Glu Ile
1               5                   10                  15

Leu Leu Lys Gly Leu Glu Lys Leu Glu Tyr Arg Gly Tyr Asp Ser Ala
            20                  25                  30

Gly Leu Ala Phe Val Asn Asp Gly Val Gln Val His Lys Glu Val Gly
        35                  40                  45

Arg Ile Ala Ala Leu Arg Glu Val Val Pro Ala Glu Ala Asp Gly Leu
    50                  55                  60

Val Gly Ile Gly His Thr Arg Trp Ala Thr His Gly Val Pro Ser Val
65                  70                  75                  80

Pro Asn Ala His Pro His Gln Ser Ala Ser Ser Arg Phe Thr Leu Val
                85                  90                  95

His Asn Gly Val Ile Glu Asn Asp Glu Gln Leu Lys Ala Glu Leu Asn
            100                 105                 110

Val Asp Leu Leu Ser Asp Thr Asp Thr Glu Val Ile Val Gln Met Ile
        115                 120                 125

Glu Lys Asn Phe Ala Glu Thr Asn Asp Val Val Glu Ala Phe Arg Gln
    130                 135                 140

Thr Leu Arg Val Leu His Gly Ser Tyr Ala Leu Ala Leu Ile Asp Ala
145                 150                 155                 160

Glu Asn Pro Asp Val Leu Tyr Val Ala Lys Asn Lys Ser Pro Leu Leu
                165                 170                 175

Val Gly Leu Gly Asp Gly Thr Phe Asn Val Val Ala Ser Asp Ala Met
            180                 185                 190

Ala Met Leu Gln Val Thr Asp Gln Phe Val Glu Leu His Asp Gly Glu
        195                 200                 205

Met Ile Ile Leu Thr Arg Asp Ser Val Thr Ile Gln Asp Leu Asp Gly
    210                 215                 220

Asn Val Lys Glu Arg Glu Ala Tyr Thr Ala Glu Ile Asp Ala Ser Asp
```

```
225                     230                     235                     240

Ile Glu Lys Gly Thr Tyr Ala His Tyr Met Leu Lys Glu Met Asp Glu
                245                     250                     255

Gln Pro Ala Val Ile Arg Asn Ile Val Gln Lys Tyr Gln Asn Glu Ser
                260                     265                     270

Gly Glu Ile Thr Leu Asp Gln Ser Val Arg Asp Leu Val Leu Gly Arg
                275                     280                     285

Asp Arg Val Tyr Ile Ile Gly Cys Gly Thr Ser Tyr His Ala Gly Leu
                290                     295                     300

Ile Gly Lys Gln Leu Ile Glu Gln Ile Ala Gly Ile Pro Thr Glu Val
305                     310                     315                     320

His Ile Ser Ser Glu Phe Gly Tyr Asn Met Pro Leu Leu Thr Glu Lys
                325                     330                     335

Pro Leu Phe Leu Phe Leu Ser Gln Ser Gly Glu Thr Ala Asp Ser Arg
                340                     345                     350

Ala Val Leu Val Glu Ala Lys Lys Leu Gly His Pro Ala Leu Thr Ile
                355                     360                     365

Thr Asn Val Ala Gly Ser Thr Leu Ser Arg Glu Ala Asn Ala Thr Leu
                370                     375                     380

Leu Leu His Ala Gly Pro Glu Ile Ala Val Ala Ser Thr Lys Ala Tyr
385                     390                     395                     400

Thr Ala Gln Ile Ala Val Leu Ala Val Leu Ala Phe Asp Leu Ala Gln
                405                     410                     415

Ala Lys Gly Val Asp Val Asn Phe Asp Leu Met Lys Glu Leu Gly Lys
                420                     425                     430

Ile Ser Ser Ala Met Glu Ser Val Met Ser Gln Lys Glu Arg Phe Gln
                435                     440                     445

Glu Ile Ala Ser Glu Tyr Leu Ser Glu Ser Arg Asn Ala Phe Phe Ile
                450                     455                     460

Gly Arg Gly Gln Asp Ala Tyr Val Gly Met Glu Gly Ala Leu Lys Leu
465                     470                     475                     480

Lys Glu Ile Ser Tyr Ile Gln Ala Glu Gly Tyr Ala Gly Gly Glu Leu
                485                     490                     495

Lys His Gly Pro Ile Ala Leu Ile Glu Asp Asn Thr Pro Val Ile Ala
                500                     505                     510

Leu Val Thr Gln Pro His Val His Leu Asn Asn Arg Gly Asn Val Lys
                515                     520                     525

Glu Val Val Ala Arg Gly Ala Asn Ala Cys Val Ile Ala Ala Glu Gly
                530                     535                     540

Leu Glu Leu Pro Thr Asp Ala Phe Val Ile Pro Ala Val Glu Pro Leu
545                     550                     555                     560

Leu Ser Pro Leu Leu Ser Val Leu Pro Leu Gln Leu Ile Ser Tyr Tyr
                565                     570                     575

Ala Ala Leu Gly Arg Asp Cys Asp Val Asp Lys Pro Arg Asn Leu Ala
                580                     585                     590

Lys Ser Val Thr Val Glu
                595
```

```
<210> SEQ ID NO 6
<211> LENGTH: 1797
<212> TYPE: DNA
<213> ORGANISM: Exiguobacterium sibiricum
<220> FEATURE:
<221> NAME/KEY: misc_feature
<223> OTHER INFORMATION: Es2 Variant
```

<400> SEQUENCE: 6

```
atgtgcggta tcgttggtat gatcggtcag gttaacacca aagaaatcct gctgaaaggt        60
ctggaaaaac tggaataccg tggttacgac tctgctggtc tggctttcgt taacgacggt       120
gttcaggttc acaaagaagt tggtcgtatc gctgctctgc gtgaagttgt tccggctgaa       180
gctgacggtc tggttggtat cggtcacacc cgttgggcta cccacggtgt tccgtctgtt       240
ccgaacgctc acccgcacca gtctgcttct tctcgtttca ccctggttca caacggtgtt       300
atcgaaaacg acgaacagct gaaagctgaa ctgaacgttg acctgctgtc tgacaccgac       360
accgaagtta tcgttcagat gatcgaaaaa aacttcgctg aaaccaacga tgttgttgaa       420
gcgttccgtc agaccctccg tgttctgcac ggttcttacg ctctggctct gatcgacgct       480
gaaaacccgg acgttctgta cgttgctaaa aacaaatctc cgctgctggt tggtctgggt       540
gacggtacct tcaacgttgt tgcttctgac gctatggcta tgctgcaggt taccgaccag       600
ttcgttgaac tgcacgacgg tgaaatgatc atcctgaccc gtgactctgt taccatccag       660
gacctggacg gtaacgttaa agaacgtgaa gcttacaccg ctgaaatcga cgcttctgac       720
atcgaaaaag gtacctacgc tcactacatg ctgaaagaaa tggacgaaca gccggctgtt       780
atccgtaaca tcgttcagaa ataccagaac gaatctggtg aaatcaccct ggaccagtct       840
gttcgtgacc tggttctggg tagggaccgt gtatacatca tcggctgcgg tacctcttac       900
cacgctggtc tgatcggtaa acagctgatc gaacagatcg ctggtatccc gaccgaagtt       960
cacatctctt ctgaattcgg ttacaacatg ccgctgctga ccgaaaaacc gctgttcctg      1020
ttcctgtctc agtctggtga aaccgctgac tctcgtgctg ttctggttga agctaaaaaa      1080
ctgggtcacc cggctctgac catcaccaac gttgctggtt ctaccctgtc tcgtgaagct      1140
aacgctaccc tgctgctgca cgctggtccg gaaatcgctg ttgcttctac caaagcttac      1200
accgctcaga tcgctgttct ggctgttctg gctttcgacc tggctcaggc taaaggtgtt      1260
gacgttaact tcgacctgat gaaagaactg ggtaaaatct cttctgctat ggaatctgtt      1320
atgtctcaga agaacgtttt ccaggaaatc gcttctgaat acctgtctga atctcgtaac      1380
gctttcttca tcggtcgtgg tcaggacgct tacgttggta tggaaggtgc tctgaaactg      1440
aaagaaatct cttacatcca ggctgaaggt tacgctggtg gtgaactgaa acacggtccg      1500
atcgctctga tcgaagacaa cacccccggtt atcgctctgg ttacccagcc gcacgttcac      1560
ctgaacaacc gtggtaacgt taaagaagtt gttgctcgtg gtgctaacgc ttgcgttatc      1620
gctgctgaag tctggaact gccgaccgac gctttcgtta tcccggctgt tgaaccgctg      1680
ctgtctccgc tgctgtctgt tctgccgctg cagctgatct cttactacgc tgctctgggt      1740
cgtgactgcg acgttgacaa accgcgtaac ctggctaaat ctgttaccgt tgaataa       1797
```

<210> SEQ ID NO 7
<211> LENGTH: 253
<212> TYPE: PRT
<213> ORGANISM: Clostridium nexile

<400> SEQUENCE: 7

```
Met Gly Lys Gln Lys Lys Glu Lys Lys Gly Met Lys Ile Ile Lys Thr
1               5                   10                  15

Ala Asp Tyr Asn Glu Met Ser Arg Lys Ala Ala Asn Leu Ile Gly Ala
            20                  25                  30

Gln Val Ile Met Lys Pro Asn Cys Ile Leu Gly Leu Ala Thr Gly Ser
        35                  40                  45
```

```
Ser Pro Ile Gly Thr Tyr Lys Glu Leu Ile Lys Arg Cys Glu Glu Gly
    50              55              60

Asp Leu Asp Phe Ser Gln Val Lys Ser Val Asn Leu Asp Glu Tyr Lys
65              70              75              80

Gly Leu Pro Arg Asp Asn Asp Gln Ser Tyr Tyr Tyr Phe Met Asn His
            85              90              95

Asn Leu Phe Asp His Ile Asn Ile Asp Lys Ala Asn Thr His Val Pro
            100             105             110

Asn Gly Met Glu Pro Asp Ala Ala Lys Glu Cys Ala Asn Tyr Glu Glu
        115             120             125

Leu Ile Lys Ser Leu Gly Gly Val Asp Leu Gln Leu Leu Gly Leu Gly
    130             135             140

His Asn Gly His Ile Gly Phe Asn Glu Pro Ala Glu Glu Phe Asp Lys
145             150             155             160

Val Thr His Cys Val Asp Leu Gln Glu Ser Thr Ile Glu Ala Asn Lys
            165             170             175

Arg Phe Phe Glu Ser Ala Asp Asp Val Pro Arg Gln Ala Tyr Thr Met
            180             185             190

Gly Ile Gly Thr Ile Met Ser Ala Lys Lys Ile Val Val Val Val Ser
            195             200             205

Gly Glu Asp Lys Ala Asp Ile Val Lys Arg Ala Phe Ser Gly Pro Val
    210             215             220

Thr Pro Ser Val Pro Ala Ser Ile Leu Gln Met His Pro Asp Val Thr
225             230             235             240

Val Ile Cys Asp Ala Ala Ala Tyr Ser Lys Val Glu Ala
            245             250
```

```
<210> SEQ ID NO 8
<211> LENGTH: 762
<212> TYPE: DNA
<213> ORGANISM: Clostridium nexile

<400> SEQUENCE: 8
atgggtaaac agaaaaaaga aaaaaaaggt atgaaaatca tcaaaaccgc tgactacaac      60
gaaatgtctc gtaaagctgc taacctgatc ggtgctcagg ttatcatgaa accgaactgc     120
atcctgggtc tggctaccgg ttcttctccg atcggtacct acaagaact  gatcaaacgt     180 tgcgaagaag gtgacctgga cttctctcag gttaaatctg ttaacctgga cgaatacaaa     240
ggtctgccgc gtgacaacga ccagtcttac tactacttca tgaaccacaa cctgttcgac     300
cacatcaaca tcgacaaagc taacacccac gttccgaacg gtatggaacc ggacgctgct     360
aaagaatgcg ctaactacga gaactgatc  aaatctctgg gtggtgttga cctgcagctg     420
ctgggtctgg gtcacaacgg ccatatcggc ttcaacgaac cggcggaaga attcgacaaa     480
gttacccact cgttgacct  gcaggaatct accatcgaag ctaacaaacg tttcttcgaa     540
tctgctgacg acgttccgcg tcaggcttac actatgggta tcggtaccat catgtctgct     600
aaaaaaatcg ttgttgttgt ttctggtgaa gacaaagctg acatcgttaa acgtgctttc     660
tctggtccgg ttaccccgtc tgttccggct tctatcctgc agatgcaccc ggacgttacc     720
gttatctgcg acgctgctgc ttactctaaa gttgaagctt aa                        762
```

```
<210> SEQ ID NO 9
<211> LENGTH: 658
<212> TYPE: PRT
<213> ORGANISM: Dyadobacter fermentans
```

<400> SEQUENCE: 9

Met Ser Gln Gln Thr Val Ser Pro Gln Thr Ile Leu Met Gln Ala Ser
1               5                   10                  15

Ser Asn Gly Lys Gly Thr Thr Gly Thr Ile Gly Gln Pro Ile Thr Tyr
                20                  25                  30

Glu Lys Ile Pro Thr Gln Ile Phe Ala Asp Ser Lys Glu Ala Ser Tyr
            35                  40                  45

Ala Val Ala Lys Glu Ile Ser Asp Leu Ile Arg Gln Lys Gln Lys Glu
        50                  55                  60

Gly Lys Pro Cys Val Leu Gly Leu Ala Thr Gly Ser Ser Pro Lys Thr
65                  70                  75                  80

Val Tyr Ala Ile Leu Val Arg Met His Arg Glu Glu Gly Leu Ser Phe
                85                  90                  95

Lys Asn Val Ile Ser Phe Asn Leu Asp Glu Tyr Tyr Gln Met Glu Pro
                100                 105                 110

Asp Ser Ile Tyr Ser Tyr His Arg Phe Met Lys Glu Gln Leu Phe Asp
            115                 120                 125

His Val Asp Ile Pro Lys Glu Asn Tyr Phe Leu Pro Asp Gly Thr Val
        130                 135                 140

Pro Ala Ala Leu Leu Arg Asp Tyr Cys Ala Ser Tyr Glu Asn Lys Ile
145                 150                 155                 160

Asn Ala Val Gly Gly Leu Asp Phe Gln Leu Leu Gly Ile Gly Gly Asn
                165                 170                 175

Gly His Ile Gly Phe Asn Glu Pro Gly Ser Leu Ile Asn Ser His Thr
            180                 185                 190

Arg Leu Ile Thr Leu Asp His Ser Thr Arg Ala Ala Ala Ser Met Glu
            195                 200                 205

Phe Gly Gly Leu His Asn Val Pro Arg Lys Ala Ile Thr Leu Gly Val
        210                 215                 220

Ala Pro Ile Leu Asn Ala Arg Arg Val Val Leu Leu Ala Trp Gly Glu
225                 230                 235                 240

Arg Lys Ala Gln Val Ile Lys Gly Ala Val Glu Gly Pro Val Thr Glu
                245                 250                 255

Leu Asn Pro Ala Ser Tyr Leu Gln Ala His Ala Asp Val Ser Phe Val
                260                 265                 270

Val Asp Glu Ser Ala Ala Ser Glu Leu Thr Arg Ile Lys Thr Pro Trp
            275                 280                 285

Ala Val Asp Ser Val Ile Trp Asp Asn Lys Met Ile Lys Lys Ala Val
        290                 295                 300

Thr His Leu Ser Gln Thr Leu Lys Lys Pro Ile Leu Lys Leu Thr Asp
305                 310                 315                 320

Lys Asp Tyr Asn Asp Asn Gly Met Ser Asp Leu Leu Ala Gln Tyr Gly
            325                 330                 335

Ala Gly Tyr Glu Ile Asn Ile Asn Val Phe Asn Gln Leu Gln His Thr
            340                 345                 350

Ile Thr Gly Trp Pro Gly Gly Lys Pro Asn Ala Asp Asp Thr His Arg
            355                 360                 365

Pro Glu Arg Ala Gln Pro Lys Lys Arg Val Leu Ile Phe Ser Pro
        370                 375                 380

His Pro Asp Asp Asp Ile Ile Ser Met Gly Gly Thr Phe Gln Arg Leu
385                 390                 395                 400

Val Asp Gln Gly His Glu Val His Val Ala Tyr Gln Thr Ser Gly Asn

```
                    405              410              415
Ile Ala Val Ala Asp Asp Glu Ala Leu Arg Phe Ile Asp Phe Val Val
            420              425              430

Asp Phe Asn Thr Gly Phe Asp Ile Glu Ser Pro Asn Ala Asn Lys Leu
            435              440              445

Phe Leu Asp Ala Lys Glu Phe Leu Arg His Thr Lys Asn Ser Glu Ile
        450              455              460

Asp Ser Pro Glu Val Arg Lys Val Lys Gly Leu Ile Arg Arg Gly Glu
465              470              475              480

Ala Lys Ala Thr Cys Arg Phe Val Gly Ile Pro Thr Ser Gln Ala His
                485              490              495

Phe Leu Asp Met Pro Phe Tyr Glu Thr Gly Thr Val Gln Lys Lys Pro
            500              505              510

Ile Gly Glu Glu Asp Ile Lys Ile Ile Glu Asn Leu Ile Glu Glu Val
            515              520              525

Lys Pro His Gln Ile Tyr Ala Ala Gly Asp Phe Ala Asp Pro His Gly
        530              535              540

Thr His Lys Val Cys Trp Asp Ala Ile Glu Ala Ala Leu Gln Arg Ser
545              550              555              560

Lys His Lys Asn Phe Met Lys Asp Cys Trp Val Trp Leu Tyr Arg Gly
                565              570              575

Ala Trp Ala Glu Trp Asp Ile Tyr Glu Ile Glu Met Ala Val Pro Met
            580              585              590

Ser Pro Asp Gln Val Leu Lys Lys Arg Gln Gly Ile Phe Lys His Gln
            595              600              605

Ser Gln Lys Asp Gly Val Val Phe Gln Gly Glu Asp Ser Arg Glu Phe
        610              615              620

Trp Gln Arg Ala Glu Glu Arg Asn Arg Gly Thr Ala Gln Leu Tyr Asp
625              630              635              640

Ser Leu Gly Leu Ala Glu Tyr Glu Ala Met Glu Ala Phe Val Arg Trp
                645              650              655

Lys Phe
```

<210> SEQ ID NO 10
<211> LENGTH: 1977
<212> TYPE: DNA
<213> ORGANISM: Dyadobacter fermentans

<400> SEQUENCE: 10

```
atgtctcagc aaaccgtaag cccgcagacc atcctgatgc aggcttcttc taacggtaaa      60
ggtaccaccg gtaccatcgg tcagccgatc acctacgaaa aaatcccgac ccagatcttc     120
gctgactcta agaagcttc ttacgctgtt gctaaagaaa tctctgacct gatccgtcag     180
aaacagaaag aaggtaaacc gtgcgttctg ggtctggcta ccggttcttc tcccaagacc     240
gtatacgcaa tcctggttcg tatgcaccgt gaagaaggtc tgtctttcaa aaacgttatc     300
tctttcaacc tggacgaata ctaccagatg gaaccggact ctatctactc ttaccaccgt     360
ttcatgaaag aacagctgtt cgaccacgtt gacatcccga agaaaacta cttcctgccg     420 gacggtaccg ttccggctgc tctgctgcgt gactactgcg cttcttacga aaacaaaatc     480
aacgctgttg gtggtctgga cttccagctg ctgggtatcg gtggtaacgg ccatatcggc     540
ttcaacgaac cgggctctct gatcaactct cacaccccgtc tgatcaccct ggaccactct     600
acccgtgctg ctgcttctat ggaattcggt ggtctgcaca acgttccgcg taaagctatc     660
```

-continued

```
accctgggtg ttgctccgat cctgaacgct cgtcgtgttg ttctgctggc ttggggtgaa      720
cgtaaagctc aggttatcaa aggtgctgtt gaaggtccgg ttaccgaact gaacccggct      780
tcttacctgc aggctcacgc tgacgtttct ttcgttgttg acgaatctgc tgcttctgaa      840
ctgacccgta tcaaaacccc gtgggctgtt gactctgtta tctgggacaa caaaatgatc      900
aaaaaagctg ttacccacct gtctcagacc ctgaaaaaac cgatcctgaa actgaccgac      960
aaagactaca cgacaacgg tatgtctgac ctgctggctc agtacggtgc tggttacgaa     1020
ataaatatca acgtgttcaa ccaactgcag cacaccatca ccggttggcc gggtggtaaa     1080
ccgaacgctg acgacaccca ccgtccggaa cgtgctcagc cggctaaaaa acgtgttctg     1140
atcttctctc cgcacccgga cgacgacatc atctctatgg gtggtacctt ccagcgtctg     1200
gttgaccagg gtcacgaagt tcacgttgct taccagacct ctggtaacat cgctgttgct     1260
gacgacgaag ctctgcgttt tatcgacttc gttgttgact ttaacaccgg cttcgacatc     1320
gaatcgccga acgctaacaa actgttcctg gacgctaaag aattcctgcg tcacaccaaa     1380
aactctgaaa tcgactctcc ggaagttcgt aaagttaaag gtctgatccg tcgtggtgaa     1440
gctaaagcta cctgccgttt cgttggtatc ccgacctctc aggctcactt cctggacatg     1500
ccgttctacg aaaccggtac cgttcagaaa aaaccgatcg gtgaagaaga catcaaaatc     1560
atcgaaaacc tgatcgaaga agttaaaccg caccagatct acgctgctgg tgacttcgct     1620
gacccgcacg gtacccacaa agtttgctgg gacgctatcg aagctgctct gcagcgttct     1680
aaacacaaaa acttcatgaa agactgctgg gtttggctgt accgtggtgc ttgggctgaa     1740
tgggacatct acgaaatcga aatggctgtt ccgatgtctc cggaccaggt tctgaaaaaa     1800
cgtcagggta tcttcaaaca ccagtctcag aaagacggcg ttgtattcca gggcgaagac     1860
tctcgtgaat ctggcagcg tgctgaagaa cgtaaccgtg gtaccgctca gctgtacgac     1920
tctctgggtc tggctgaata cgaagctatg gaagctttcg ttcgttggaa attctaa      1977
```

```
<210> SEQ ID NO 11
<211> LENGTH: 249
<212> TYPE: PRT
<213> ORGANISM: Pedobacter heparinus
<220> FEATURE:
<221> NAME/KEY: misc_feature
<223> OTHER INFORMATION: Ph1 variant

<400> SEQUENCE: 11

Met Thr Ile Lys Met Glu Thr Ser Val Thr Asn Asn Pro Val Glu Leu
1               5                   10                  15

Gly Lys Ala Ala Gly Lys Ala Ala Ala Ala Leu Ile Arg Glu Thr Ile
                20                  25                  30

Ala Lys Asn Gly Lys Ala Asn Ile Ile Leu Ala Thr Gly Ala Ser Gln
            35                  40                  45

Phe Glu Thr Leu Asn Gln Leu Ile Ser Glu Glu Ile Asp Trp Ser Lys
        50                  55                  60

Val Thr Met Phe His Leu Asp Glu Tyr Ile Gly Leu Ser Glu Ser Ala
65                  70                  75                  80

Pro Ala Ser Phe Arg Lys Tyr Leu Lys Glu Arg Phe Leu Glu Lys Val
                85                  90                  95

Ser Pro Leu Lys Ala Ala Tyr Leu Val Asn Gly Glu Thr Asp Pro Glu
            100                 105                 110

Ala Glu Cys Gln Arg Leu Gly Glu Ile Ile Thr Gln Asn Pro Ile Asp
        115                 120                 125
```

-continued

```
Val Ala Leu Val Gly Ile Gly Glu Asn Gly His Leu Ala Phe Asn Asp
    130             135             140

Pro Pro Ala Asp Phe Glu Thr Lys Arg Pro Tyr Leu Val Val Asn Leu
145             150             155             160

Asp Glu Gln Cys Arg Arg Gln Gln Phe Gly Glu Gly Trp Phe Lys Thr
                165             170             175

Ile Glu Glu Val Pro Thr Gln Ala Ile Ser Met Ser Val Gln Gln Ile
            180             185             190

Leu Lys Ser Lys His Ile Ile Cys Ser Val Pro Asp Ser Arg Lys Ala
        195             200             205

Gln Ala Val Lys Asp Ser Leu Glu Gln Pro Val Ser Asn Gln Tyr Pro
    210             215             220

Ser Ser Ile Leu Gln Leu His Pro Asp Cys Arg Phe Phe Phe Asp Lys
225             230             235             240

Ala Ser Ala Glu Leu Leu Ser Glu Ala
            245
```

```
<210> SEQ ID NO 12
<211> LENGTH: 750
<212> TYPE: DNA
<213> ORGANISM: Pedobacter heparinus
<220> FEATURE:
<221> NAME/KEY: misc_feature
<223> OTHER INFORMATION: Ph1 variant

<400> SEQUENCE: 12
atgaccatca aaatggaaac ctctgttacc aacaacccgg ttgaactggg taaagctgct      60
ggtaaagctg ctgctgctct gatccgtgaa accatcgcta aaaacggtaa agctaacatc     120
atcctggcta ccggtgcttc tcagttcgaa accctgaacc agctgatctc tgaagaaatc     180
gactggtcta aagttaccat gttccacctg gacgaataca tcggtctgtc tgaatctgct     240
ccagcgagct tccgtaaata cctcaaagaa cgtttcctgg aaaaagtttc tccgctgaaa     300
gctgcttacc tggttaacgg tgaaaccgac ccggaagctg aatgccagcg tctgggtgaa     360
atcatcaccc agaacccgat cgacgttgct ctggttggta tcggtgaaaa cggccatctg     420
gcgttcaacg acccgccagc tgacttcgaa accaaacgtc cgtacctggt tgttaacctg     480
gacgaacagt gccgtcgtca gcagttcggt gaaggttggt tcaaaaccat cgaagaagtt     540
ccgacccagg ctatctctat gtctgttcag cagatcctga atctaaaca catcatctgc      600 tctgttccgg actctcgtaa agctcaggct gttaaagact ctctggagca accggtaagc     660
aaccagtacc cgtcttctat cctgcagctg cacccggact gccgtttctt cttcgacaaa     720
gcttctgctg aactgctgtc tgaagcttaa                                       750
```

```
<210> SEQ ID NO 13
<211> LENGTH: 254
<212> TYPE: PRT
<213> ORGANISM: Pedobacter heparinus
<220> FEATURE:
<221> NAME/KEY: misc_feature
<223> OTHER INFORMATION: Ph2 variant

<400> SEQUENCE: 13

Met Ile Lys Glu Phe Leu Lys Asp Lys Leu Lys Val Lys Val Tyr Asn
1               5               10              15

Thr Arg Gly Glu Met Gly Thr Ser Ala Ala Asp Leu Ala Ala Gln Cys
            20              25              30

Leu Arg Glu Leu Leu Gln His Lys Asp Glu Val Asn Ile Ile Phe Ala
```

```
                35              40              45
Ala Ala Ala Ser Gln Asn Glu Phe Leu Glu Ala Ile Ala Val Glu Lys
    50              55              60

Asp Ile Ala Trp Asn Arg Val Asn Ala Phe His Met Asp Glu Tyr Thr
65              70              75              80

Gly Leu Pro Val Thr His Pro Gln Arg Phe Gly Asn Phe Leu Asn Lys
                85              90              95

Lys Ile Phe Ser Lys Leu Pro Leu Lys Lys Val Tyr Tyr Leu Asn Glu
            100             105             110

Asp Gly Asn Asp Thr Glu Ala Glu Ser Arg Arg Tyr Ala Ala Leu Leu
        115             120             125

Glu Lys Met Pro Pro Asp Ile Thr Phe Met Gly Ile Gly Glu Asn Thr
    130             135             140

His Leu Ala Phe Asn Asp Pro His Val Ala Asp Phe Asn Asp Pro Val
145             150             155             160

Leu Val Lys Ile Ile Asp Leu Asp Glu Pro Cys Lys Val Gln Gln Val
            165             170             175

His Asp Gly Cys Phe Pro Thr Val Ala Glu Val Pro Ser Leu Ala Tyr
        180             185             190

Thr Leu Thr Ile Pro Ala Leu Leu Gln Ser Lys Tyr Ile Phe Cys Met
    195             200             205

Val Pro Gly Lys Asn Lys Ala Gln Ala Val Lys Tyr Thr Leu Asn Glu
    210             215             220

Ser Ile Thr Ala Lys Tyr Pro Ser Thr Ser Leu Arg Thr His Ser Asp
225             230             235             240

Ala Thr Leu Phe Leu Asp Gln Asp Ser Ala Ser Leu Ile Leu
            245             250
```

<210> SEQ ID NO 14
<211> LENGTH: 765
<212> TYPE: DNA
<213> ORGANISM: Pedobacter heparinus
<220> FEATURE:
<221> NAME/KEY: misc_feature
<223> OTHER INFORMATION: Ph2 variant

<400> SEQUENCE: 14

```
atgatcaaag aattcctgaa agacaaactg aaagttaaag tttacaacac ccgtggtgaa      60
atgggtacct ctgctgctga cctggctgct cagtgcctgc gtgaactgct gcagcacaaa     120
gacgaagtta acatcatctt cgctgctgct gcttctcaga cgaattcct  ggaagctatc     180 gctgttgaaa aagacatcgc ttggaaccgt gttaacgctt ccacatgga  cgaatacacc     240 ggtctgccag ttacccatcc gcagaggttc ggtaacttcc tcaacaaaaa aatcttctct     300
aaactgccgc tgaaaaaagt ttactacctg aacgaagacg gtaacgacac cgaagctgaa     360
tctcgtcgtt acgctgctct gctggaaaaa atgccgccgg acatcacctt catgggtatc     420
ggtgaaaaca cccacctggc tttcaacgac ccgcacgttg ctgacttcaa cgacccggtt     480
ctggttaaaa tcatcgacct ggacgaaccg tgcaaagttc agcaggttca cgacggttgc     540
ttcccgaccg ttgctgaagt tccgtctctg gcttacaccc tgaccatccc ggctctgctg     600
cagtctaaat acatcttctg catggttccg ggtaaaaaca aagctcaggc tgttaaatac     660
accctgaacg aatctatcac cgctaaatac ccgtctacct ctctgcgtac ccactctgac     720
gctaccctgt tcctggacca ggactctgct tctctgatcc tgtaa                     765
```

```
<210> SEQ ID NO 15
<211> LENGTH: 639
<212> TYPE: PRT
<213> ORGANISM: Pedobacter heparinus
<220> FEATURE:
<221> NAME/KEY: misc_feature
<223> OTHER INFORMATION: Ph3 variant

<400> SEQUENCE: 15

Met Ala Arg Leu Asn Leu Leu Glu Glu Thr Arg Phe Glu Lys Leu Pro
1               5                   10                  15

Val Ser Val Phe Glu Asn Pro Lys Glu Ala Ser Leu Ser Val Ala His
            20                  25                  30

Arg Ile Gly Asn Leu Ile Lys Glu Lys Gln Lys Asn Asn Ala Gln Ala
        35                  40                  45

Val Leu Gly Leu Ala Thr Gly Ala Thr Pro Ile Ala Val Tyr Ala Glu
    50                  55                  60

Leu Val Arg Met His Arg Glu Glu Gly Leu Ser Phe Lys Asn Val Val
65                  70                  75                  80

Thr Phe Asn Leu Asp Glu Tyr Tyr Pro Met Gln Pro Asn Ala Ala Gln
                85                  90                  95

Ser Tyr Val Thr Phe Met Asn Glu Asn Leu Phe Asp His Ile Asp Ile
            100                 105                 110

Asp Lys Lys Asn Val Asn Ile Pro Asp Gly Thr Leu Ser Leu Glu Glu
        115                 120                 125

Ile Pro Ala Phe Cys Leu Asn Tyr Glu Lys Lys Ile Gly Asp Leu Gly
    130                 135                 140

Gly Leu Asp Ile Gln Ile Leu Gly Ile Gly Arg Thr Gly His Ile Gly
145                 150                 155                 160

Phe Asn Glu Pro Gly Ser Ala Pro Asn Ser Gly Thr Arg Leu Val Thr
                165                 170                 175

Leu Asp Asp Leu Thr Arg Arg Asp Ala Ala Arg Asp Phe Gly Gly Lys
                180                 185                 190

Ser Phe Val Pro Thr Lys Ala Ile Thr Met Gly Val Gly Thr Ile Phe
            195                 200                 205

Lys Ala Arg Glu Ile Ile Leu Met Ala Trp Asn Lys Lys Lys Ala Pro
    210                 215                 220

Ile Ile Lys Lys Thr Val Glu Gly Glu Ile Ser Ser Glu Val Pro Ala
225                 230                 235                 240

Thr Tyr Leu Gln Leu Ser Asp Asn Val Glu Phe Ile Leu Asp Lys Asp
                245                 250                 255

Ala Ala Ser Leu Leu Thr Arg Phe Asp Thr Pro Trp Leu Val Lys Asp
            260                 265                 270

Cys Ile Trp Asp Glu Lys Leu Thr Arg Lys Ala Val Ile Trp Leu Ala
        275                 280                 285

Asn Thr Leu Lys Lys Pro Val Leu Lys Leu Thr Glu Asp Asp Tyr Asn
    290                 295                 300

Asn Asn Gly Met Ala Gln Leu Ala Val Glu Gln Gly Pro Val Tyr Asn
305                 310                 315                 320

Ile Asn Ile His Ile Phe Asn Lys Leu Gln His Thr Ile Thr Gly Trp
                325                 330                 335

Pro Gly Gly Lys Pro Asn Ala Asp Asp Ser Gln Arg Pro Glu Arg Ala
            340                 345                 350

Glu Pro Ala Lys Lys Arg Ser Ile Ile Phe Ser Pro His Pro Asp Asp
            355                 360                 365
```

-continued

```
Asp Val Ile Ser Met Gly Gly Thr Phe Ile Arg Leu Val Asp Gln Gln
    370             375                 380

Gln Asp Val His Val Ala Tyr Gln Thr Ser Gly Asn Thr Ala Val Trp
385             390                 395                 400

Asp Asp Asp Ala Leu Arg Phe Val Glu Phe Asn Ile Asp Phe Ser Glu
            405                 410                 415

Lys Met Gly Leu Glu Thr Ala Glu Leu Lys Lys Leu Tyr Gln Asn Met
            420                 425                 430

Arg Ser Phe Ile Glu Gln Lys Lys Pro Asn Gln Ile Asp Thr Pro Glu
            435                 440                 445

Ile Gln Thr Val Lys Gly Leu Ile Arg Lys Gly Glu Ala Ile Ala Gly
    450                 455                 460

Ala Arg Tyr Cys Gly Leu Ala Asp Asp His Ile His Phe Met Ala Leu
465             470                 475                 480

Pro Phe Tyr Glu Ser Gly Lys Ser Gln Lys Asn Pro Val Thr Asp Ala
            485                 490                 495

Asp Val Val Leu Thr Met Glu Leu Leu Gln Lys Val Lys Pro His Gln
            500                 505                 510

Val Phe Ala Ala Gly Asp Phe Glu Asp Pro His Gly Thr His Ile Val
    515                 520                 525

Cys Phe Asn Ile Ile Leu Glu Ala Leu Arg Arg Leu Ser Lys Thr Glu
    530                 535                 540

Ala Trp Val Lys Asp Cys Trp Leu Trp Met Tyr Arg Gly Ala Trp Gln
545             550                 555                 560

Glu Phe Glu Thr Tyr Glu Ile Glu Met Ala Val Pro Leu Ser Pro Gln
            565                 570                 575

Glu Val Glu Arg Lys Lys Phe Ala Ile Phe Lys His Gln Ser Gln Lys
            580                 585                 590

Asp Arg Ala Val Phe Pro Gly Asp Asp Ala Arg Glu Phe Trp Gln Arg
            595                 600                 605

Ala Glu Asp Arg Asn Arg Glu Thr Ala Gln Ala Tyr Asp Ser Leu Gly
    610                 615                 620

Leu Ala Glu Tyr Glu Ala Met Glu Ala Phe Val Arg Tyr Lys Phe
625                 630                 635
```

<210> SEQ ID NO 16
<211> LENGTH: 1920
<212> TYPE: DNA
<213> ORGANISM: Pedobacter heparinus
<220> FEATURE:
<221> NAME/KEY: misc_feature
<223> OTHER INFORMATION: Ph3 variant

<400> SEQUENCE: 16

```
atggctcgtc tgaacctgct ggaagaaacc cgtttcgaaa aactgccggt ttctgttttc     60
gaaaacccga agaagcttc tctgtctgtt gctcaccgta tcggtaacct gatcaaagaa    120
aaacagaaaa acaacgctca ggctgttctg ggtctggcta ccggtgctac cccaatagct    180
gtgtacgcag aactggttcg tatgcaccgt gaagaaggtc tgtctttcaa aaacgttgtt    240
accttcaacc tggacgaata ctacccgatg cagccgaacg ctgctcagtc ttacgttacc    300
ttcatgaacg aaaacctgtt cgaccacatc gacatcgaca aaaaaaacgt taacatcccg    360
gacggtaccc tgtctctgga agaaatcccg gctttctgcc tgaactacga aaaaaaaatc    420
ggtgacctgg gtggtctgga catccagatc ctgggtatcg tcgtaccgg tcatataggc    480 ttcaacgaac cgggctctgc tccgaactct ggtaccgtc tggttaccct ggacgacctg    540
```

```
acccgtcgtg acgctgctcg tgacttcggt ggtaaatctt tcgttccgac caaagctatc      600
actatgggtg ttggtaccat cttcaaagct cgtgaaatca tcctgatggc ttggaacaaa      660
aaaaaagctc cgatcatcaa aaaaaccgtt gaaggtgaaa tctcttctga agttccggct      720
acctacctgc agctgtctga caacgttgaa ttcatcctgg acaaagacgc tgcttctctg      780
ctgacccgtt tcgacacccc gtggctggtt aaagactgca tctgggacga aaaactgacc      840
cgtaaagctg ttatctggct ggctaacacc ctgaaaaaac cggttctgaa actgaccgaa      900
gacgactaca acaacaacgg tatggctcag ctggctgttg aacagggtcc ggtttacaac      960
atcaacatcc acatcttcaa caaactgcag cacaccatca ccggttggcc gggtggtaaa     1020
ccgaacgctg acgactctca gcgtccggaa cgtgctgaac cggctaaaaa acgttctatc     1080
atcttctctc cgcacccgga cgacgacgtt atctctatgg gtggtacctt catccgtctg     1140
gttgaccagc agcaggacgt tcacgttgct taccagacct ctggtaacac cgctgtttgg     1200
gacgacgacg ctctgcgttt cgttgaattc aacatcgact tctctgaaaa aatgggtctg     1260
gaaaccgctg aactgaaaaa actgtaccag aacatgcgta gcttcatcga acagaagaaa     1320
ccgaaccaga tcgacacccc ggaaatccag accgttaaag gtctgatccg taaaggtgaa     1380
gctatcgctg gtgctcgtta ctgcggtctg gctgacgacc acatccactt catggctctg     1440
ccgttctacg aatctggtaa atctcagaaa aacccggtta ccgacgctga cgttgttctg     1500
actatggaac tgctgcagaa agttaaaccg caccaggttt tcgctgctgg tgacttcgaa     1560
gacccgcacg gtacccacat cgtttgcttc aacatcatcc tggaagctct gcgtcgtctg     1620
tctaaaaccg aagcttgggt taaagactgc tggctgtgga tgtaccgtgg tgcttggcag     1680
gaattcgaaa cctacgaaat cgaaatggct gttccgctgt ctccgcagga agttgaacgt     1740
aaaaaattcg ctatcttcaa acaccagtct cagaaagacc gtgctgtttt cccgggtgac     1800
gacgctcgtg aattctggca gcgtgctgaa gaccgtaacc gtgaaaccgc tcaggcttac     1860
gactctctgg gtctggctga atacgaagct atggaagctt tcgttcgtta caaattctaa     1920
```

```
<210> SEQ ID NO 17
<211> LENGTH: 172
<212> TYPE: PRT
<213> ORGANISM: Granulicella tundricola

<400> SEQUENCE: 17

Met Arg Thr Gly Ser His Gly Trp Ser Asp His Gly Gln Ala Leu Arg
1               5                   10                  15

Lys Gln Ala Ile Val Asp Ala Leu Ser Leu Gly Val Ala Lys His His
            20                  25                  30

Pro Arg Asp Leu Arg Leu Phe Ala Ala Val Leu Glu Lys Asn Asn Phe
        35                  40                  45

Ala Gly Gln Asp Ile Ala Gln Ile Ala Phe Glu Gln Leu Ser Ser Arg
    50                  55                  60

Phe Asp Gln Tyr Leu Gly Arg Leu Tyr Arg Glu Lys Gly Asp Lys Gln
65                  70                  75                  80

Arg Gly Leu Ile Leu Phe Asp Lys Ser Ser Thr Glu Arg Arg Ile Gln
                85                  90                  95

Thr Leu Ala Arg Asp Phe Lys His Thr Gly His Ser Phe Gly Ile Thr
            100                 105                 110

Arg Asn Tyr Ala Glu Val Pro Val Phe Leu Asp Ser Arg Ala Ser Arg
        115                 120                 125
```

```
Leu Ile Gln Leu Ala Asp Leu Val Ala Tyr Ala Ile Phe Arg His His
    130             135             140

Glu His Gly Asp Ser Thr Tyr Tyr Asn Ala Cys Ser His Cys Phe Asp
145             150             155             160

Ala Glu Gly Gly Val Val His Gly Leu Tyr Val Arg
            165             170
```

```
<210> SEQ ID NO 18
<211> LENGTH: 519
<212> TYPE: DNA
<213> ORGANISM: Granulicella tundricola

<400> SEQUENCE: 18
atgcgtaccg gttctcacgg ttggtctgac cacggtcagg ctctgcgtaa acaggctatc      60
gttgacgctc tgtctctggg tgttgctaaa caccacccgc gtgacctgcg tctgttcgct     120
gctgttctgg aaaaaaacaa cttcgctggt caggacatcg ctcagatcgc tttcgaacag     180
ctgtcttctc gtttcgacca gtacctgggt cgtctgtacc gtgaaaaagg tgacaaacag     240
cgtggtctga tcctgttcga caaatcttct accgaacgtc gtatccagac cctggctcgt     300
gacttcaaac acaccggtca ctctttcggt atcaccagaa actacgctga agttccggta     360
ttcctggaca gccgtgcttc tcgtctgatc cagctggctg acctggttgc ttacgctatc     420
ttccgtcacc acgaacacgg tgactctacc tactacaacg cttgctctca ctgcttcgac     480
gctgaaggtg gtgttgttca cggtctgtac gttcgttaa                            519
```

```
<210> SEQ ID NO 19
<211> LENGTH: 629
<212> TYPE: PRT
<213> ORGANISM: Terriglobus roseus

<400> SEQUENCE: 19

Met Cys Gly Ile Val Gly Tyr Ile Gly Ala Arg Pro Ala Val Pro Val
1               5               10              15

Ile Met Asp Gly Leu Arg Arg Leu Glu Tyr Arg Gly Tyr Asp Ser Ala
                20              25              30

Gly Ile Ala Leu Gly Gly Ala Asp Thr Gly Leu Ser Ile Arg Arg Ala
            35              40              45

Ser Gly Lys Leu Arg Asn Leu Glu Ser Ser Leu Ser Leu Asn Pro Leu
    50              55              60

Gln Gly Asp Tyr Gly Ile Gly His Thr Arg Trp Ala Thr His Gly Arg
65              70              75              80

Pro Ser Glu Thr Asn Ala His Pro His Arg Asp Cys Thr Gly Ser Leu
                85              90              95

Val Val Val His Asn Gly Ile Val Glu Asn Tyr Cys Glu Leu Gln Asp
            100             105             110

Gln Leu Lys Ala Lys Gly His Phe Phe Leu Thr Glu Thr Asp Thr Glu
        115             120             125

Ile Ile Ala His Leu Ile Glu Gln Glu Tyr Leu Asp Leu Arg Glu Arg
    130             135             140

Asn Asp Gly Asp Ala Ala Pro Ser Leu Glu Lys Ala Val Ser Gln Ala
145             150             155             160

Val Lys Lys Leu Thr Gly Ala Phe Ala Ile Gly Val Ile Ser Thr Asp
                165             170             175

Asp Pro Gly Lys Leu Val Ala Ala Arg Ser Gly Pro Pro Ala Val Val
            180             185             190
```

-continued

```
Gly Phe Gly Asp Gly Glu Tyr Phe Leu Ala Ser Asp Val Pro Gly Ile
        195                 200                 205

Leu Gln Tyr Thr Arg Asp Ile Val Phe Leu Gln Asp Gly Asp Val Ala
    210                 215                 220

Val Leu Thr Arg Ser Gly Ile Ser Phe Ser Asp Phe His Gly Lys Pro
225                 230                 235                 240

Leu Lys Arg Ser Pro Gln His Ile Thr Trp Asp Pro Ile Gln Ala Glu
                245                 250                 255

Lys Asn Gly Tyr Ala His Phe Met Leu Lys Glu Ile Tyr Glu Gln Pro
            260                 265                 270

Arg Ala Val Arg Asp Thr Leu Arg Gly Arg Ile Ser Ala Ala Ser Gly
            275                 280                 285

His Ile Glu Leu Pro Gly Leu Asp Leu Ser His Asp Glu Ile Val His
        290                 295                 300

Ala Glu Arg Ile Leu Ile Ala Ser Cys Gly Thr Ser Trp His Ala Gly
305                 310                 315                 320

Leu Val Gly Lys Phe Leu Leu Glu Arg Met Val Arg Ile Pro Val Glu
                325                 330                 335

Val Asp Tyr Ala Ser Glu Phe Arg Tyr Arg Arg Pro Ile Met Arg Ser
            340                 345                 350

Arg Asp Ile Gly Leu Leu Ile Ser Gln Ser Gly Glu Thr Ala Asp Thr
            355                 360                 365

Leu Ala Ala Gln Leu Glu Met Ile Ala Gly Asp Ile Pro Thr Leu Ser
        370                 375                 380

Ile Cys Asn Val Val Asp Ala Ala Leu Thr Arg Lys Ala Arg Gly Ser
385                 390                 395                 400

Ile Thr Thr Asn Ala Gly Pro Glu Ile Gly Val Ala Ser Thr Lys Ala
                405                 410                 415

Phe Thr Ala Gln Ile Ala Ala Leu Leu Thr Leu Ser Leu Tyr Phe Ala
            420                 425                 430

Gln Cys Arg Lys Thr Met Pro Gln Glu Ala Val Gln Ser Ile Leu Arg
            435                 440                 445

Glu Leu Glu Val Leu Pro Lys Ala Met Glu Glu Ala Leu Arg Thr Ser
        450                 455                 460

Ala Pro Val Cys Ala Arg Leu Ala Lys Ile Phe Ser Asn Ala Thr Asp
465                 470                 475                 480

Val Leu Phe Leu Gly Arg Gly Ile His Tyr Pro Ile Ala Leu Glu Gly
                485                 490                 495

Ala Leu Lys Leu Lys Glu Ile Ser Tyr Ile His Ala Glu Gly Tyr Pro
            500                 505                 510

Ala Gly Glu Met Lys His Gly Pro Asn Ala Leu Ile Asp Glu Thr Leu
            515                 520                 525

Pro Val Val Cys Leu Ala Thr Lys Asp Gly Asp Asp Pro Asp Ser Val
        530                 535                 540

Leu Lys Tyr Glu Lys Thr Leu Ser Asn Ile Gln Glu Val Thr Ala Arg
545                 550                 555                 560

Gly Gly Arg Val Ile Ala Ile Val Val Glu Gly Asp Thr Ala Val Ser
            565                 570                 575

Ser Leu Val Glu His Thr Ile Thr Ile Pro Arg Ala Ser Glu Ala Leu
            580                 585                 590

Leu Pro Ile Leu Glu Thr Val Pro Leu Gln Leu Leu Ala Tyr Phe Ile
        595                 600                 605

Ala Val Glu Lys Gly Cys Asp Val Asp Gln Pro Arg Asn Leu Ala Lys
```

-continued

|  | 610 | 615 | 620 |
|---|---|---|---|

Ser Val Thr Val Glu
625

<210> SEQ ID NO 20
<211> LENGTH: 1890
<212> TYPE: DNA
<213> ORGANISM: Terriglobus roseus

<400> SEQUENCE: 20

```
atgtgcggta tcgttggtta catcggtgct cgtccggctg ttccggttat catggacggt      60
ctgcgtcgtc tggaataccg tggttacgac tctgctggta tcgctctggg tggtgctgac     120
accggtctgt ctatccgtcg tgcttctggt aaactgcgta acctggaatc ttctctgtct     180
ctgaacccgc tgcagggtga ctacggtatc ggtcacaccc gttgggctac ccacggtcgt     240
ccgtctgaaa ccaacgctca cccgcaccgt gactgcaccg ttctctggt tgttgttcac      300 aacggtatcg ttgaaaacta ctgcgaactg caggaccagc tgaaagctaa aggtcacttc     360
ttcctgaccg aaaccgacac cgaaatcatc gctcacctga tcgaacagga atacctggac     420
ctgcgtgaac gtaacgacgg tgacgctgct ccgtctctgg aaaaagctgt ttctcaggct     480
gttaaaaaac tgaccggtgc tttcgctatc ggtgttatct ctaccgacga cccgggtaaa     540
ctggttgctg ctcgttctgg tccgccggct gttgttggtt tcggtgacgg tgaatacttc     600
ctggcttctg acgttccggg tatcctgcag tacactcgtg acatcgtctt cctgcaagac     660
ggtgacgttg ctgttctgac ccgttctggt atctctttct ctgacttcca cggtaaaccg     720
ctgaaacgtt ctccgcagca catcacctgg gacccgatcc aggctgaaaa aaacggttac     780
gctcacttca tgctgaaaga aatctacgaa cagccgcgtg ctgttcgtga caccctgcgt     840
ggtcgtatct ctgctgcttc tggtcacatc gaactgccgg tctggacct gtctcacgac      900 gaaatcgttc acgctgaacg tatcctgatc gcttcttgcg gtacctcttg gcacgctggt     960
ctggttggta aattcctgct ggaacgtatg gttcgtatcc cggttgaagt tgactacgct    1020
tctgaattcc gttaccgtcg tccgatcatg cgttctcgtg acatcggtct gctgatctct    1080
cagtctggtg aaaccgctga cacccctggct gctcagctgg aaatgatcgc tggtgacatc    1140
ccgaccctgt ctatctgcaa cgttgttgac gctgctctga cccgtaaagc tcgtggttct    1200
atcaccacca acgctggtcc ggaaatcggt gttgcttcta ctaaggcgtt caccgctcag    1260
atagctgctc tgctgaccct gtctctgtac ttcgctcagt gccgtaaaac catgccgcag    1320
gaagctgttc agtctatcct gcgtgaactg gaagttctgc cgaaagctat ggaagaagct    1380
ctgcgtacct ctgctccggt ttgcgctcgt ctggctaaaa tcttctctaa cgctaccgac    1440
gttctgttcc tgggtcgtgg tatccactac ccgatcgctc tggaaggtgc tctgaaactg    1500
aaagaaatct cttacatcca cgctgaaggt tacccggctg gtgaaatgaa acacggtccg    1560
aacgctctga tcgacgaaac cctgccggtt gtttgcctgg ctaccaaaga cggtgacgac    1620
ccggactctg ttctgaaata cgaaaaaacc ctgtctaaca tccaggaagt taccgctcgt    1680
ggtggtcgtg ttatcgctat cgttgttgaa ggtgacaccg ctgtttcttc tctggttgaa    1740
cacaccatca ccatcccgcg tgcttctgaa gctctgctgc cgatcctgga aaccgttccg    1800
ctgcagctgc tggcttactt catcgctgtt gaaaaaggtt gcgacgttga ccagccgcgt    1860
aacctggcta atctgttac cgttgaataa                                       1890
```

<210> SEQ ID NO 21

-continued

```
<211> LENGTH: 294
<212> TYPE: PRT
<213> ORGANISM: Akkermansia muciniphila

<400> SEQUENCE: 21

Met Arg Ala Ala Pro Arg Lys Ala Val Gly Arg Val Glu Ala Ser Val
1               5                   10                  15

Pro Trp Asp Phe Ser Arg Lys Tyr Ala Ala Val His His Ser Gly Thr
                20                  25                  30

Ile Ser Val Glu Asn Ala Arg Lys Arg Ser Lys Ile Gly Arg Val Met
            35                  40                  45

Lys Val Glu Thr Phe Glu Thr Pro Gln Asp Ala Ala Lys Ala Leu Ala
        50                  55                  60

Gly Glu Val Ala Glu Leu Ile Arg Thr Arg Ala Ala Glu Gly Lys Asn
65                  70                  75                  80

Val Val Leu Gly Leu Ala Thr Gly Ala Thr Pro Leu Pro Phe Tyr Ala
                85                  90                  95

Glu Leu Val Arg Met His Lys Glu Glu Gly Leu Ser Phe Ala Asn Val
            100                 105                 110

Ile Ser Phe Asn Leu Asp Glu Tyr Ser Gly Leu Asp Arg Asp His Pro
            115                 120                 125

Glu Ser Tyr Trp Tyr Phe Met His Thr Asn Leu Phe Asn His Ile Asp
        130                 135                 140

Ile Lys Pro Glu Asn Ile Asn Leu Pro Ser Gly Thr Val Lys Asp Asp
145                 150                 155                 160

Glu Ile Ala Ala His Cys Ala Ala Tyr Glu Gln Lys Ile Lys Asp Cys
                165                 170                 175

Gly Gly Ile Asp Leu Gln Ile Leu Gly Ile Gly Arg Thr Gly His Ile
            180                 185                 190

Gly Phe Asn Glu Pro Gly Ser Asp Asp Thr Thr Val Thr Arg Gln Val
            195                 200                 205

His Leu Asp Glu Leu Thr Arg Ser Asp Ala Ala Pro Ala Phe Gly Gly
        210                 215                 220

Ile Glu Asn Val Pro Thr Thr Ala Ile Thr Met Gly Val Ala Thr Ile
225                 230                 235                 240

Met Gly Ala Arg Glu Val Ala Leu Met Ala Trp Gly Glu Lys Lys Ala
                245                 250                 255

Ser Ile Val Lys Lys Ala Val Gln Gly Pro Val Thr Val Asp Val Ala
            260                 265                 270

Ala Ser Tyr Leu Gln Lys His Pro Asn Ala Lys Phe Leu Leu Asp Lys
        275                 280                 285

Gly Ala Ala Ser Leu Leu
    290

<210> SEQ ID NO 22
<211> LENGTH: 885
<212> TYPE: DNA
<213> ORGANISM: Akkermansia muciniphila

<400> SEQUENCE: 22
atgcgtgctg ctccgcgtaa agctgttggt cgtgttgaag cttctgttcc gtgggacttc      60
tctcgtaaat acgctgctgt tcaccactct ggtaccatct ctgttgaaaa cgctcgtaaa     120
cgttctaaaa tcggtcgtgt tatgaaagtt gaaaccttcg aaacccccgca ggacgctgct     180 aaagctctgg ctggtgaagt tgctgaactg atccgtaccc gtgctgctga aggtaaaaac     240
```

```
gttgttctgg gtctggctac cggtgctacc ccgctgccgt tctacgctga actggttcgt      300
atgcacaaag aagaaggtct gtctttcgct aacgttatct ctttcaacct ggacgaatac      360
tctggtctgg accgtgacca cccggaatct tactggtact tcatgcacac caacctgttc      420
aaccacatcg acatcaaacc ggaaaacatc aacctgccgt ctggtaccgt taaagacgac      480
gaaatcgctg ctcactgcgc tgcttacgaa cagaaaatca agactgcgg tggtatcgac       540 ctgcagatcc tgggtatcgg tcgtaccggt catataggct tcaacgaacc gggctctgac      600
gacaccaccg ttacccgtca ggttcacctg gacgaactga cccgttctga cgctgcccct      660
gcgttcggtg gtatcgagaa cgttccgacc accgctatca ctatgggtgt tgctaccatc      720
atgggtgctc gtgaagttgc tctgatggct tggggtgaaa aaaaagcttc tatcgttaaa      780
aaagctgttc agggtccggt taccgttgac gttgctgctt cttacctgca gaaacacccg      840
aacgctaaat tcctgctgga caaaggtgct gcttctctgc tgtaa                       885
```

```
<210> SEQ ID NO 23
<211> LENGTH: 270
<212> TYPE: PRT
<213> ORGANISM: Bifidobacterium longum
<220> FEATURE:
<221> NAME/KEY: misc_feature
<223> OTHER INFORMATION: B11 variant

<400> SEQUENCE: 23

Met Pro Glu Ile Ile Ile Val Lys Asn Glu Ala Glu Ala Gly Glu Ile
1               5                   10                  15

Tyr Gly Arg Cys Val Ala Asp Leu Ile Lys Ala Lys Pro Asp Ala Val
                20                  25                  30

Leu Gly Leu Ala Thr Gly Ser Ser Pro Leu Ala Ala Tyr Gln Ala Leu
            35                  40                  45

Ala Lys Ile Val Lys Asp Glu Ala Ile Asp Val Ser Gly Val Arg Gly
        50                  55                  60

Phe Ala Leu Asp Glu Tyr Ile Gly Leu Pro Leu Thr His Pro Glu Ser
65                  70                  75                  80

Tyr His Ala Thr Ile His Arg Thr Val Val Glu Pro Leu Gly Leu Asp
                85                  90                  95

Pro Ala Lys Val His Val Pro Gly Asp Val Leu Asn Gly Thr Pro Leu
            100                 105                 110

Glu Asp Gly Asp Lys Val Ala Leu Ala Gly Pro Ala Tyr Asp Arg Ala
        115                 120                 125

Ile Glu Ala Ala Gly Gly Ile Asp Val Gln Ile Leu Gly Ile Gly Thr
        130                 135                 140

Asp Gly His Val Gly Phe Asn Glu Pro Gly Ser Ser Leu Ala Ser Gly
145                 150                 155                 160

Thr Arg Val Lys Thr Leu Ala Glu Gln Thr Arg Val Asp Asn Ala Arg
                165                 170                 175

Phe Phe Asp Asn Asp Ile Asn Gln Val Pro Thr His Cys Ile Thr Gln
            180                 185                 190

Gly Ile Gly Thr Ile Met Lys Ala Arg His Leu Val Leu Leu Ala Phe
        195                 200                 205

Gly Ala Gly Lys Ala Glu Ala Ile Glu Glu Thr Val Glu Gly Gly Leu
        210                 215                 220

Ser Ala Phe Cys Pro Ala Ser Ala Leu Gln Met His Pro His Ala Thr
225                 230                 235                 240

Ile Ile Val Asp Glu Glu Ala Ala Ser Arg Leu Arg His Lys Asp Tyr
```

```
                    245               250               255
        Tyr Arg Tyr Ala Tyr Thr His Lys Pro Ala Trp Gln Gly Ile
                260               265               270
```

<210> SEQ ID NO 24
<211> LENGTH: 813
<212> TYPE: DNA
<213> ORGANISM: Bifidobacterium longum
<220> FEATURE:
<221> NAME/KEY: misc_feature
<223> OTHER INFORMATION: B11 variant

<400> SEQUENCE: 24

```
atgccggaaa tcatcatcgt taaaaacgaa gctgaagctg gtgaaatcta cggtcgttgc      60
gttgctgacc tgatcaaagc taaaccggac gctgttctgg gtctggctac cggttcttct     120
ccgctggctg cttaccaggc tctggctaaa atcgttaaag acgaagctat cgacgtttct     180
ggtgttcgtg gtttcgctct ggacgaatac atcggtctgc cgctgaccca cccggaatct     240
taccacgcta ccatccaccg taccgttgtt gaaccgctgg gtctggaccc ggctaaagtt     300
cacgttccgg gtgacgttct gaacggtacc ccgctggaag acggtgacaa agttgctctg     360
gctggtccgg cttacgaccg tgctatcgaa gctgctggtg gtatcgacgt tcagatcctg     420
ggtatcggta ccgacggtca tgtaggcttc aacgaaccgg ctcttctct ggcttctggt      480 acccgtgtta aaaccctggc tgaacagacc cgtgttgaca atgcgaggtt cttcgacaac     540
gacatcaacc aggttccgac ccactgcatc acccagggta tcggtaccat catgaaagct     600
cgtcacctgg ttctgctggc tttcggtgct ggtaaagctg aagctatcga agaaaccgtt     660
gaaggtggtc tgtctgcttt ctgcccggct tctgctctgc agatgcaccc gcacgctacc     720
atcatcgttg acgaagaagc tgcttctcgt ctgcgtcaca agactacta ccgttacgct       780 tacacccaca aaccggcttg gcagggtatc taa                                   813
```

<210> SEQ ID NO 25
<211> LENGTH: 270
<212> TYPE: PRT
<213> ORGANISM: Bifidobacterium longum
<220> FEATURE:
<221> NAME/KEY: misc_feature
<223> OTHER INFORMATION: B12 variant

<400> SEQUENCE: 25

```
Met Pro Glu Ile Ile Ile Val Lys Asn Glu Ala Glu Ala Gly Glu Ile
1               5                   10                  15

Tyr Gly Arg Cys Val Ala Asp Leu Ile Lys Ala Lys Pro Asp Ala Val
            20                  25                  30

Leu Gly Leu Ala Thr Gly Ser Ser Pro Leu Ala Ala Tyr Gln Ala Leu
        35                  40                  45

Ala Lys Ile Val Lys Asp Glu Ala Ile Asp Val Ser Gly Val Arg Gly
    50                  55                  60

Phe Ala Leu Asp Glu Tyr Ile Gly Leu Pro Leu Thr His Pro Glu Ser
65                  70                  75                  80

Tyr His Ala Thr Ile His Arg Thr Val Val Glu Pro Leu Gly Leu Asp
                85                  90                  95

Pro Ala Lys Val His Val Pro Gly Asp Val Leu Asn Gly Thr Pro Leu
            100                 105                 110

Glu Asp Gly Asp Lys Val Ala Leu Ala Gly Pro Ala Tyr Asp Arg Ala
            115                 120                 125
```

-continued

```
Ile Glu Ala Ala Gly Gly Ile Asp Val Gln Ile Leu Gly Ile Gly Thr
    130             135             140

Asp Gly His Val Gly Phe Asn Glu Pro Gly Ser Ser Leu Ala Ser Gly
145             150             155             160

Thr Arg Val Lys Thr Leu Ala Glu Gln Thr Arg Val Asp Asn Ala Arg
                165             170             175

Phe Phe Asp Asn Asp Ile Asn Gln Val Pro Thr His Cys Ile Thr Gln
                180             185             190

Gly Ile Gly Thr Ile Met Lys Ala Arg His Leu Val Leu Leu Ala Phe
            195             200             205

Gly Ala Gly Lys Ala Glu Ala Ile Glu Glu Thr Val Glu Gly Gly Leu
    210             215             220

Ser Ala Phe Cys Pro Ala Ser Ala Leu Gln Met His Pro His Ala Thr
225             230             235             240

Ile Ile Val Asp Glu Glu Ala Ala Ser Arg Leu Arg His Lys Asp Tyr
                245             250             255

Tyr Arg Tyr Ala Tyr Thr His Lys Pro Ala Trp Gln Gly Ile
            260             265             270
```

```
<210> SEQ ID NO 26
<211> LENGTH: 813
<212> TYPE: DNA
<213> ORGANISM: Bifidobacterium longum
<220> FEATURE:
<221> NAME/KEY: misc_feature
<223> OTHER INFORMATION: B12 variant

<400> SEQUENCE: 26
atgccggaaa tcatcatcgt taaaaacgaa gctgaagctg gtgaaatcta cggtcgttgc      60
gttgctgacc tgatcaaagc taaaccggac gctgttctgg gtctggctac cggttcttct     120
ccgctggctg cttaccaggc tctggctaaa atcgttaaag acgaagctat cgacgtttct     180
ggtgttcgtg gtttcgctct ggacgaatac atcggtctgc cgctgaccca cccggaatct     240
taccacgcta ccatccaccg taccgttgtt gaaccgctgg gtctggaccc ggctaaagtt     300
cacgttccgg gtgacgttct gaacggtacc ccgctggaag acggtgacaa agttgctctg     360
gctggtccgg cttacgaccg tgctatcgaa gctgctggtg gtatcgacgt tcagatcctg     420
ggtatcggta ccgacggtca gtaggcttc aacgaaccgg gctcttctct ggcttctggt      480
acccgtgtta aaaccctggc tgaacagacc cgtgttgaca tgcgaggtt cttcgacaac      540 gacatcaacc aggttccgac ccactgcatc acccagggta tcggtaccat catgaaagct     600
cgtcacctgg ttctgctggc tttcggtgct ggtaaagctg aagctatcga agaaaccgtt     660
gaaggtggtc tgtctgcttt ctgcccggct tctgctctgc agatgcaccc gcacgctacc     720
atcatcgttg acgaagaagc tgcttctcgt ctgcgtcaca agactacta ccgttacgct      780 tacacccaca aaccggcttg gcagggtatc taa                                  813
```

```
<210> SEQ ID NO 27
<211> LENGTH: 242
<212> TYPE: PRT
<213> ORGANISM: Myxobacterium xanthis

<400> SEQUENCE: 27

Met Arg Ile Arg Val Phe Asp Ser Glu Arg Glu Ala Ala Ala Thr Cys
1               5               10              15

Ala Gln Arg Ile Ala Arg Ala Ala Ala Ala His Pro Ser Leu Val Leu
            20              25              30
```

```
Gly Leu Pro Thr Gly Arg Thr Pro Leu Asn Val Tyr Arg Glu Leu Val
        35                  40                  45

Glu Leu Phe Thr Arg Gly Gly Leu Asp Trp Ala Gln Val Arg Thr Phe
    50                  55                  60

Asn Leu Asp Glu Phe Leu Gly Val Ser Ala Asp Asp Ala Gly Ser Phe
65                  70                  75                  80

Arg Ala Tyr Met Glu Arg His Leu Phe Gln His Val Asn Leu Ser Pro
                85                  90                  95

Ala His Ile Gln Phe Leu Asp Gly Ala Val Glu Asp Ala Glu Ala Glu
            100                 105                 110

Cys Ala Arg Tyr Glu Ala Arg Leu Ala Glu Ala Gly Gly Leu Asp Leu
        115                 120                 125

Val Leu Leu Gly Leu Gly Ser Asn Gly His Leu Ala Phe Asn Glu Pro
    130                 135                 140

Ala Asp Gly Leu Arg Ala Arg Cys His Arg Thr Arg Leu Ser Arg Gln
145                 150                 155                 160

Thr Arg Glu Ala Asn Leu Met Leu Phe Gly Asp Asp Pro Ser Arg Val
                165                 170                 175

Pro Met Glu Ala Leu Thr Leu Gly Met Ala Ser Ile Leu Gln Ala Arg
            180                 185                 190

Gln Ala Leu Leu Leu Ala Phe Gly Glu Ala Lys Ala Glu Ala Val Arg
        195                 200                 205

Gly Met Val Glu Gly Pro Val Ser Pro Arg Cys Pro Ala Ser Phe Leu
    210                 215                 220

Gln Leu His Pro Asp Val Glu Val Trp Leu Asp Pro Ala Ala Ala Arg
225                 230                 235                 240

Ala Leu
```

<210> SEQ ID NO 28
<211> LENGTH: 729
<212> TYPE: DNA
<213> ORGANISM: Myxobacterium xanthis

<400> SEQUENCE: 28

```
atgcgtatcc gtgttttcga ctctgaacgt gaagctgctg ctacctgcgc tcagcgtatc      60
gctcgtgctg ctgctgctca cccgtctctg gttctgggtc tgccgaccgg tcgtaccccg     120
ctgaacgttt accgtgaact ggttgaactg ttcacccgtg gtggtctgga ctgggctcag     180
gttcgtacct tcaacctgga cgaatttctc ggtgtaagcg ctgacgacgc tggttctttc     240
cgtgcttaca tggaacgtca cctgttccag cacgttaacc tgtctccggc tcacatccag     300
ttcctggacg gtgctgttga agacgctgaa gctgaatgcg ctcgttacga agctcgtctg     360
gctgaagctg gtggtctgga cctggttctg ctgggtctgg gttctaacgg tcacctggct     420
ttcaacgaac cggctgacgg tctgcgtgct cgttgccacc gtacccgtct gtctcgtcag     480
acccgtgaag ctaacctgat gctgttcggt gacgacccgt ctcgtgttcc gatggaagct     540
ctgaccctgg gtatggcttc tatcctgcag gctcgtcagg ctctgctgct ggctttcggt     600
gaagctaaag ctgaagctgt cgtggtatg gttgaaggtc cggtttctcc gcgttgccca     660
gctagcttcc tgcagctgca tccggacgtt gaagtttggc tggacccggc tgctgctcgt     720
gctctgtaa                                                             729
```

<210> SEQ ID NO 29
<211> LENGTH: 369

-continued

```
<212> TYPE: PRT
<213> ORGANISM: Stackebrandtia nassauensis
<220> FEATURE:
<221> NAME/KEY: misc_feature
<223> OTHER INFORMATION: Sn1 variant

<400> SEQUENCE: 29

Met Ser Gln Gln Gln Ala Ala Arg Ser Thr Thr Ala Gly Ala Thr Asp
1               5                   10                  15

Ala Thr Ala Ala Thr Pro Pro Gly Ala Gly Met Ala Ala Asp Ile Ala
            20                  25                  30

Asp Gln Pro Glu Ala Phe Ala Arg Leu Ala Glu Thr Gln Ser Gly Ala
        35                  40                  45

Ile Ala Asp Ile Ala Ala Glu Ile Ala Arg Glu Arg Pro Arg Phe Val
    50                  55                  60

Met Phe Thr Ala Arg Gly Thr Ser Asp His Ala Ala Leu Tyr Ala Ala
65                  70                  75                  80

Tyr Leu Thr Glu Ile Arg Leu Gly Ile Pro Ala Gly Leu Ala Ser Pro
                85                  90                  95

Ser Ala Ile Thr Val Tyr Gly Ala Arg Pro Asp Leu Ser Glu Ala Leu
            100                 105                 110

Val Val Gly Val Ser Gln Ser Gly Gly Ser Pro Asp Ile Ala Glu Val
            115                 120                 125

Leu Arg Val Ala Ser Glu Ser Gly Ala Arg Thr Leu Ala Val Thr Asn
    130                 135                 140

Asn Pro Glu Ser Pro Leu Ala Lys Gln Ala Gly Leu Asn Ile Asp Val
145                 150                 155                 160

Ser Ala Gly His Glu Lys Ala Val Ala Ala Thr Lys Thr Tyr Thr Ala
                165                 170                 175

Glu Leu Leu Ala Leu Phe Met Leu Ile Glu Gly Ile Arg Ala Gly Asp
            180                 185                 190

Gly Lys Leu Ala Gly Asp Glu Ala Ala Ala Val Ala Ala Leu Pro Glu
            195                 200                 205

Leu Ala Arg Thr Val Leu Ala Asp Glu Thr Pro Val Gln Leu Ala Ala
    210                 215                 220

Arg Tyr Arg Phe Ala Glu Arg Leu Val Thr Thr Gly Arg Gly Tyr Ala
225                 230                 235                 240

Tyr Pro Thr Ala Arg Glu Thr Ala Leu Lys Leu Met Glu Thr Ser Tyr
                245                 250                 255

Leu Ser Ala Leu Ser Phe Ser Gly Ala Asp Leu Leu His Gly Pro Leu
            260                 265                 270

Ala Met Ala Asp Pro Asp Ile Pro Val Leu Ala Ile Val Gly Asp Gly
            275                 280                 285

Pro Gly Gly Asn Ala Met Arg Asp Val Ile Gly Arg Leu Gly Glu Arg
    290                 295                 300

Arg Ala Asp Val Val Ser Ile Gly Ala Ser Asp Val Glu Gly Ala Pro
305                 310                 315                 320

Ile Arg Ile Pro Val Pro Ala Val Asp Glu Arg Leu Ala Pro Met Leu
                325                 330                 335

Asp Ile Leu Pro Leu Gln Arg Leu Ala Leu Ala Leu Ala Leu Asn Arg
            340                 345                 350

Gly Glu Asn Pro Asp Ala Pro Arg Gly Leu Arg Lys Val Thr Glu Thr
            355                 360                 365

Leu
```

<210> SEQ ID NO 30
<211> LENGTH: 1110
<212> TYPE: DNA
<213> ORGANISM: Stackebrandtia nassauensis
<220> FEATURE:
<221> NAME/KEY: misc_feature
<223> OTHER INFORMATION: Sn1 variant

<400> SEQUENCE: 30
atgtctcagc agcaggctgc tcgttctacc accgctggtg ctaccgacgc taccgctgct        60
accccgccgg gtgctggtat ggctgctgac atcgctgacc agccggaagc tttcgctcgt       120
ctggctgaaa cccagtctgg tgctatcgct gacatcgctg ctgaaatcgc tcgtgaacgt       180
ccgcgtttcg ttatgttcac cgctcgtggt acctctgacc acgctgctct gtacgctgct       240
tacctgaccg aaatccgtct gggtatcccg gctggtctgg cttctccgtc tgctatcacc       300
gtttacggtg ctcgtccgga cctgtctgaa gctctggttg ttggtgtttc tcagtctggt       360
ggttctccgg acatcgctga agttctgcgt gttgcttctg aatctggtgc tcgtaccctg       420
gctgttacca acaacccgga atctccgctg gctaaacagg ctggtctgaa catcgacgtt       480
tctgctggtc acgaaaaagc tgttgctgct accaaaacct acaccgctga actgctggct       540
ctgttcatgc tgatcgaagg tatccgtgct ggtgacggta aactggctgg tgacgaagct       600
gctgctgttg ctgctctgcc ggaactggct cgtaccgttc tggctgacga accccggtt       660 cagctggctg ctcgttaccg tttcgctgaa cgtctggtta ccaccggtcg tggttacgct       720
tacccgaccg ctcgtgaaac cgctctgaaa ctgatggaaa cctcttacct gtctgctctg       780
tctttctctg gtgctgacct gctgcacggt ccgctggcta tggctgaccc ggacatcccg       840
gttctggcta tcgttggtga cggtccgggt ggtaacgcta tgcgtgacgt tatcggtcgt       900
ctgggtgaac gtagggctga cgttgtaagc atcggtgctt ctgacgttga aggtgctccg       960
atccgtatcc cggttccggc tgttgacgaa cgtctggctc cgatgctgga catcctgccg      1020
ctgcagcgtc tggctctggc tctggctctg aaccgtggtg aaaaacccgga cgctccgcgt      1080 ggtctgcgta aagttaccga aaccctgtaa                                       1110

<210> SEQ ID NO 31
<211> LENGTH: 289
<212> TYPE: PRT
<213> ORGANISM: Stackebrandtia nassauensis
<220> FEATURE:
<221> NAME/KEY: misc_feature
<223> OTHER INFORMATION: Sn2 variant

<400> SEQUENCE: 31

Met Ala Ile Val Asp Ala Glu Ile Ala Arg Gln Pro Glu Cys Trp Thr
1               5                   10                  15

Ala Ala Ala Glu Leu Ala Val Glu His Ala Gly Leu Phe Pro Lys Ala
            20                  25                  30

Gly Glu Arg Val Ala Val Val Gly Cys Gly Thr Ser Trp Phe Met Ala
        35                  40                  45

Gln Ala Val Ala Gly Leu Arg Glu Ala Ser Gly Ala Gly Glu Thr Asp
    50                  55                  60

Ala Phe Thr Ala Ser Glu Phe Pro Asp Arg Arg Tyr Asp Arg Leu Ile
65                  70                  75                  80

Ala Leu Ser Arg Ser Gly Thr Thr Ser Glu Val Val Glu Leu Leu Asn
                85                  90                  95

Arg Thr Asp Ile Pro Ser Leu Ala Ile Val Gly Asp Gly Asp Thr Pro

-continued

```
              100               105               110
Ala Val Ala Ala Ala Asp Ala Ala Ile Ala Met Pro Phe Ala Ser Asp
        115               120               125

Gln Ser Val Val Met Thr Ser Phe Ala Thr Ser Val Val Ala Leu Phe
    130               135               140

Arg Ala Gln Leu Gly Ile Asp Gln Ala Ala Ala Ile Ala Asp Cys Arg
145               150               155               160

Thr Ala Leu Thr Ala Glu Leu Pro Val Asp Val Ala Lys Leu Glu Gln
              165               170               175

Ile Ser Phe Ile Gly Ala Gly Trp Thr Ile Gly Leu Ala Asn Glu Ala
              180               185               190

Ala Leu Lys Ala Arg Glu Ala Ala Thr Phe Trp Ala Glu Ser Tyr Pro
        195               200               205

Ala Met Asp Tyr Arg His Gly Pro Ile Ser Ile Ala Gly Pro Asn Arg
        210               215               220

Ala Thr Trp Glu Leu Gly Pro Thr Gly Ala Gly Leu Arg Ala Glu Val
225               230               235               240

Glu Ala Thr Gly Gly Ala Phe Val Ala Ser Ser Leu Asp Pro Leu Ala
              245               250               255

Glu Leu Val Leu Ala Gln Arg Leu Ala Val Ala Leu Ala Arg Leu Arg
        260               265               270

Gly Leu Asn Pro Asp Ser Pro Arg His Leu Thr Arg Ser Val Val Leu
        275               280               285

Pro
```

```
<210> SEQ ID NO 32
<211> LENGTH: 870
<212> TYPE: DNA
<213> ORGANISM: Stackebrandtia nassauensis
<220> FEATURE:
<221> NAME/KEY: misc_feature
<223> OTHER INFORMATION: Sn2 variant

<400> SEQUENCE: 32
atggctatcg ttgacgctga aatcgctcgt cagccggaat gctggaccgc tgctgctgaa      60
ctggctgttg aacacgctgg tctgttcccg aaagctggtg aacgtgttgc tgttgttggt     120
tgcggtacct cttggttcat ggctcaggct gttgctggtc tgcgtgaagc ttctggtgct     180
ggtgaaactg acgcgttcac cgcttctgag ttcccggacc gtcgttacga ccgtctgatc     240
gctctgtctc gttctggtac cacctctgaa gttgttgaac tgctgaaccg taccgacatc     300
ccgtctctgg ctatcgttgg tgacggtgac accccggctg ttgctgctgc tgacgctgct     360
atcgctatgc cgttcgcttc tgaccagtct gttgttatga cctctttcgc tacctctgtt     420
gttgctctgt tccgtgctca gctgggtatc gaccaggctg ctgctatcgc tgactgccgt     480
accgctctga ccgctgaact gccggttgac gttgctaaac tggaacagat ctctttcatc     540
ggtgctggtt ggaccatcgg tctggctaac gaagctgctc tgaaagctcg tgaagctgct     600
accttctggg ctgaatctta cccggctatg gactaccgtc acggtccgat ctctatcgct     660
ggtccgaacc gtgctacctg gaactgggt ccgaccggtg ctggtctgcg tgctgaagtt      720
gaagctaccg gtggtgcttt cgttgcttct tctctggacc cgctggctga actggttctg     780
gctcagcgtc tggctgttgc tctggctcgt ctgcgtggtc tgaacccgga ctctccgcgt     840
cacctgaccc gttctgttgt tctgccgtaa                                       870
```

```
<210> SEQ ID NO 33
<211> LENGTH: 233
<212> TYPE: PRT
<213> ORGANISM: Artificial Sequence
<220> FEATURE:
<223> OTHER INFORMATION: Ef-Ser74Ala

<400> SEQUENCE: 33

Met Gln Ile Ile Arg Val Ala Asn Ala Glu Glu Gly Gly Lys Lys Ala
1               5                   10                  15

Phe Glu Leu Ile Lys Glu Gly Met Asn Asn Gly Ala Lys Val Leu Gly
            20                  25                  30

Leu Ala Thr Gly Ser Thr Pro Glu Thr Leu Tyr Lys Glu Met Thr Ala
        35                  40                  45

Ser Asp Ile Asp Phe Thr Glu Met Thr Ser Val Asn Leu Asp Glu Tyr
    50                  55                  60

Val Gly Leu Gly Gly Glu Asp Glu Gln Ala Tyr Arg Tyr Phe Met Asn
65                  70                  75                  80

Lys His Leu Phe Asp Lys Lys Pro Phe Lys Glu Thr Phe Val Pro Asn
                85                  90                  95

Gly Lys Ala Glu Asp Leu Asp Ala Ala Ser Ala Glu Tyr Glu Lys Ile
            100                 105                 110

Ile Asp Ala His Pro Val Asp Ile Gln Ile Leu Gly Ile Gly Gln Asn
        115                 120                 125

Gly His Ile Gly Phe Asn Glu Pro Gly Thr Pro Leu Asp Ser Leu Thr
    130                 135                 140

His Val Val Glu Leu Thr Glu Ser Thr Ile Asn Ala Asn Lys Arg Tyr
145                 150                 155                 160

Phe Asp Lys Val Glu Asp Val Pro Thr Arg Ala Val Ser Met Gly Ile
                165                 170                 175

Gly Ser Ile Met Lys Gly Lys Lys Met Ile Leu Met Ala Tyr Gly Glu
            180                 185                 190

Ala Lys Ala Glu Ala Ile Lys Gly Met Ile Asp Gly Pro Val Thr Thr
        195                 200                 205

Asp Met Pro Ala Ser Ala Leu Gln Asn His Gln Asp Val Val Val Ile
    210                 215                 220

Ile Asp Asp Ala Ala Ala Ser Lys Leu
225                 230

<210> SEQ ID NO 34
<211> LENGTH: 702
<212> TYPE: DNA
<213> ORGANISM: Artificial Sequence
<220> FEATURE:
<223> OTHER INFORMATION: Ef-Ser74Ala

<400> SEQUENCE: 34
atgcagatca tccgtgttgc taacgctgaa gaaggtggta aaaaagcttt cgaactgatc      60
aaagaaggta tgaacaacgg tgctaaagtt ctgggtctgg ctaccggttc tacccccgaa     120
accctgtaca agaaatgac cgcttctgac atcgacttca ccgaaatgac ctctgttaac     180
ctggacgaat acgttggtct gggtggtgaa gacgaacagt cttaccgtta cttcatgaac     240
aaacacctgt tcgacaaaaa accgttcaaa gaaaccttcg ttccgaacgg taaagctgaa     300
gacctggacg ctgcttctgc tgaatacgaa aaaatcatcg acgctcaccc ggttgacatc     360
cagatcctgg gtatcggtca gaacggccat atcggcttca cgaaccgggg caccccgctg     420
gactctctga cccacgttgt tgaactgacc gaatctacca tcaacgctaa caaacgttac     480
```

-continued

```
ttcgacaaag ttgaagacgt tccgacccgt gctgtttcta tgggtatcgg ttctatcatg      540
aaaggtaaaa aaatgatcct gatggcttac ggtgaagcta aagctgaagc tatcaaaggt      600
atgatcgacg tccggttac accgacatg ccggcttctg ctctgcagaa ccaccaggac        660
gttgttgtta tcatcgacga cgctgctgct tctaaactgt aa                        702
```

```
<210> SEQ ID NO 35
<211> LENGTH: 233
<212> TYPE: PRT
<213> ORGANISM: Artificial Sequence
<220> FEATURE:
<223> OTHER INFORMATION: Ef-Thr144Ala

<400> SEQUENCE: 35

Met Gln Ile Ile Arg Val Ala Asn Ala Glu Glu Gly Gly Lys Lys Ala
1               5                   10                  15

Phe Glu Leu Ile Lys Glu Gly Met Asn Asn Gly Ala Lys Val Leu Gly
                20                  25                  30

Leu Ala Thr Gly Ser Thr Pro Glu Thr Leu Tyr Lys Glu Met Thr Ala
            35                  40                  45

Ser Asp Ile Asp Phe Thr Glu Met Thr Ser Val Asn Leu Asp Glu Tyr
        50                  55                  60

Val Gly Leu Gly Gly Glu Asp Glu Gln Ser Tyr Arg Tyr Phe Met Asn
65                  70                  75                  80

Lys His Leu Phe Asp Lys Lys Pro Phe Lys Glu Thr Phe Val Pro Asn
                85                  90                  95

Gly Lys Ala Glu Asp Leu Asp Ala Ala Ser Ala Glu Tyr Glu Lys Ile
            100                 105                 110

Ile Asp Ala His Pro Val Asp Ile Gln Ile Leu Gly Ile Gly Gln Asn
        115                 120                 125

Gly His Ile Gly Phe Asn Glu Pro Gly Thr Pro Leu Asp Ser Leu Ala
        130                 135                 140

His Val Val Glu Leu Thr Glu Ser Thr Ile Asn Ala Asn Lys Arg Tyr
145                 150                 155                 160

Phe Asp Lys Val Glu Asp Val Pro Thr Arg Ala Val Ser Met Gly Ile
                165                 170                 175

Gly Ser Ile Met Lys Gly Lys Lys Met Ile Leu Met Ala Tyr Gly Glu
            180                 185                 190

Ala Lys Ala Glu Ala Ile Lys Gly Met Ile Asp Gly Pro Val Thr Thr
        195                 200                 205

Asp Met Pro Ala Ser Ala Leu Gln Asn His Gln Asp Val Val Val Ile
        210                 215                 220

Ile Asp Asp Ala Ala Ala Ser Lys Leu
225                 230
```

```
<210> SEQ ID NO 36
<211> LENGTH: 702
<212> TYPE: DNA
<213> ORGANISM: Artificial Sequence
<220> FEATURE:
<223> OTHER INFORMATION: Ef-Thr144Ala

<400> SEQUENCE: 36
atgcagatca tccgtgttgc taacgctgaa gaaggtggta aaaaagcttt cgaactgatc      60
aaagaaggta tgaacaacgg tgctaaagtt ctgggtctgg ctaccggttc taccccggaa      120
accctgtaca agaaatgac cgcttctgac atcgacttca ccgaaatgac ctctgttaac      180
```

-continued

```
ctggacgaat acgttggtct gggtggtgaa gacgaacagt cttaccgtta cttcatgaac    240
aaacacctgt tcgacaaaaa accgttcaaa gaaaccttcg ttccgaacgg taaagctgaa    300
gacctggacg ctgcttctgc tgaatacgaa aaaatcatcg acgctcaccc ggttgacatc    360
cagatcctgg gtatcggtca gaacggccat atcggcttca acgaaccggg cacccgctg    420 gactctctga cccacgttgt tgaactgacc gaatctacca tcaacgctaa caaacgttac    480
ttcgacaaag ttgaagacgt tccgacccgt gctgtttcta tgggtatcgg ttctatcatg    540
aaaggtaaaa aaatgatcct gatggcttac ggtgaagcta aagctgaagc tatcaaaggt    600
atgatcgacg gtccggttac caccgacatg ccggcttctg ctctgcagaa ccaccaggac    660
gttgttgtta tcatcgacga cgctgctgct tctaaactgt aa    702
```